United States Patent
Wenzel et al.

(10) Patent No.: US 7,718,566 B2
(45) Date of Patent: *May 18, 2010

(54) OLEFIN POLYMERIZATION CATALYSTS

(75) Inventors: Timothy T. Wenzel, Charleston, WV (US); Zondra Dee Dixon, Charleston, WV (US)

(73) Assignee: Univation Technologies, LLC, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/313,854

(22) Filed: Nov. 25, 2008

(65) Prior Publication Data

US 2009/0082195 A1 Mar. 26, 2009

Related U.S. Application Data

(60) Continuation of application No. 11/633,197, filed on Dec. 4, 2006, now Pat. No. 7,479,529, which is a division of application No. 11/193,663, filed on Jul. 29, 2005, now Pat. No. 7,163,991, which is a division of application No. 10/780,438, filed on Feb. 17, 2004, now Pat. No. 6,967,184.

(51) Int. Cl.
C08F 4/60 (2006.01)
C08F 4/606 (2006.01)
B01J 31/22 (2006.01)

(52) U.S. Cl. ............... 502/155; 502/152; 502/154; 502/167; 502/114; 526/161; 526/172; 526/113; 526/116

(58) Field of Classification Search ............ 502/152, 502/154, 155, 167; 526/161, 172, 113, 116
See application file for complete search history.

(56) References Cited

U.S. PATENT DOCUMENTS

| | | | |
|---|---|---|---|
| 4,939,217 A | 7/1990 | Stricklen | 526/114 |
| 5,318,935 A | 6/1994 | Canich et al. | 502/117 |
| 5,506,184 A | 4/1996 | Kissin et al. | 502/115 |
| 5,576,460 A | 11/1996 | Buchwald et al. | 564/386 |
| 5,889,128 A | 3/1999 | Schrock et al. | 526/107 |
| 6,248,832 B1 | 6/2001 | Peacock | 525/191 |
| 6,265,505 B1 | 7/2001 | McConville et al. | 526/161 |
| 6,271,323 B1 | 8/2001 | Loveday et al. | 526/161 |
| 6,271,325 B1 | 8/2001 | McConville et al. | 526/217 |
| 6,274,684 B1 | 8/2001 | Loveday et al. | 526/114 |
| 6,300,439 B1 | 10/2001 | McConville | 526/161 |
| 6,372,868 B1 | 4/2002 | Szul et al. | 526/114 |
| 6,417,304 B1 | 7/2002 | McConville et al. | 526/161 |
| 6,569,800 B2 | 5/2003 | Takemori et al. | 502/152 |
| 6,967,184 B2 | 11/2005 | Wenzel et al. | 502/167 |
| 7,163,991 B2 | 1/2007 | Wenzel et al. | 526/161 |
| 7,196,032 B2 | 3/2007 | Wenzel et al. | 502/17 |
| 2002/0032287 A1 | 3/2002 | McCullough | 526/68 |
| 2003/0069127 A1 | 4/2003 | Takaoki et al. | 502/108 |
| 2005/0266983 A1 | 12/2005 | Wenzel et al. | 502/150 |
| 2007/0078241 A1 | 4/2007 | Wenzel et al. | 526/161 |

FOREIGN PATENT DOCUMENTS

| | | |
|---|---|---|
| EP | 0893454 | 1/1999 |
| JP | HEI 10-330412 | 12/1998 |
| WO | WO 99/03899 | 1/1999 |
| WO | WO 02/40550 A2 | 5/2002 |
| WO | WO 02/46248 A2 | 6/2002 |
| WO | WO 02/50088 A1 | 6/2002 |
| WO | WO 02/50127 A2 | 6/2002 |
| WO | WO 02/059160 A2 | 8/2002 |

*Primary Examiner*—Caixia Lu
(74) *Attorney, Agent, or Firm*—Leandro Arechederra, III

(57) ABSTRACT

A catalyst composition and method for olefin polymerization are provided. In one aspect, the catalyst composition is represented by the formula $\alpha_a\beta_b\gamma_gMX_n$ wherein M is a metal; X is a halogenated aryloxy group; β and γ are groups that each comprise at least one Group 15 atom; α is a linking moiety that forms a chemical bond to each of β and γ; and a, b, g, and n are each integers from 1 to 4.

10 Claims, 2 Drawing Sheets

OLEFIN POLYMERIZATION CATALYSTS

CROSS REFERENCE TO RELATED APPLICATIONS

This application is a continuation application of divisional application of Ser. No. 11/633,197, filed Dec. 4, 2006, now allowed, which is a divisional application of Ser. No. 11/193,663, filed Jul. 29, 2005, issued as U.S. Pat. No. 7,163,991, which is a divisional application of Ser. No. 10/780,438, filed Feb. 17, 2004, issued as U.S. Pat. No. 6,967,184, herein incorporated by reference in their entireties.

This application is also related to Ser. No. 11/196,622, filed Aug. 3, 2005, issued as U.S. Pat. No. 7,196,032.

BACKGROUND OF THE INVENTION

1. Field of the Invention

Embodiments of the present invention generally relate to olefin polymerization catalysts. More particularly, embodiments of the present invention generally relate a catalyst system containing a metal atom bound to at least two Group 15 atoms and their use in gas or slurry phase to produce polyolefins.

2. Description of the Related Art

Advances in polymerization and catalysis have produced new polymers having improved physical and mechanical properties useful in a wide variety of products and applications. With the development of new catalysts, the choice of polymerization, such as solution, slurry, high pressure or gas phase, for producing a particular polymer has been greatly expanded. Advances in polymerization technology have also provided more efficient, highly productive and economically enhanced processes.

Metallocene catalysts have been used to produce resins having desirable product properties. While these resins have excellent toughness properties, particularly dart impact properties, these resins can be difficult to process. One approach to improve the processing of such metallocene catalyzed polyethylenes has been to blend them with another polymer. While the polymer blend tends to be more processable, the blend is expensive and adds a cumbersome step to the manufacturing process.

Another approach has been to produce two polymers together at the same time in the same reactor using two different catalysts. For example, WO 99/03899 discloses using a typical metallocene catalyst and a conventional Ziegler-Natta catalyst in the same reactor to produce a bimodal MWD HDPE. Other catalysts, such as anionic, multidentate heteroatom ligands, have also been used in mixed catalyst system. For example, U.S. Pat. No. 5,576,460 describes a preparation of arylamine ligands. U.S. Pat. No. 5,889,128 discloses a process for the living polymerization of olefins using initiators having a metal atom and a ligand having two group 15 atoms and a group 16 atom or three group 15 atoms. EP 893 454 A1 describes titanium transition metal amide compounds. U.S. Pat. No. 5,318,935 discusses amido transition metal compounds and catalyst systems for producing isotactic polypropylene. U.S. Pat. No. 5,506,184 discloses polymerization catalysts containing bidentate and tridentate ligands.

Polymers produced by two different catalysts types, however, exhibit unpredictable characteristics. The polymers produced from two different catalysts can exhibit different physical and mechanical properties compared to the individual polymers produced separately from each catalyst and blends thereof. This unpredictability may occur due to competition or other influence between the catalyst or catalyst systems used. This unpredictability may also occur due to differences in solubility of the individual catalyst components, reaction kinetics of the individual catalyst components, and the rate of decay of the individual catalyst components, just to name a few. There is a need, therefore, for a combination of compatible catalysts capable of producing polyolefin polymers having desirable combinations of processing, mechanical, and optical properties.

SUMMARY OF THE INVENTION

A compatible catalyst composition and method for olefin polymerization is provided. In one aspect, the catalyst composition is represented by the formula $\alpha_a\beta_b\gamma_g MX_n$ wherein M is a metal; X is a halogenated aryloxy group; $\beta$ and $\gamma$ are groups that each comprise at least one Group 15 atom; $\alpha$ is a linking moiety that forms a chemical bond to each of $\beta$ and $\gamma$; and a, b, g, and n are each integers from 1 to 4.

In one aspect, the method for olefin polymerization comprises combining one or more olefins with a catalyst system represented by the formula:

or

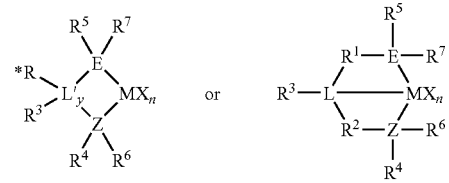

wherein M is a metal;

X is a halogenated aryloxy group;

$\beta$ and $\gamma$ are groups that each comprise at least one Group 15 atom;

$\alpha$ is a linking moiety that forms a chemical bond to each of $\beta$ and $\gamma$;

a, b, g, and n are each integers from 1 to 4;

y is 0 or 1;

L is a Group 15 element;

L' is a Group 15 element;

E is a Group 15 element;

Z is a Group 15 element;

$R^1$ and $R^2$ are independently a $C_1$ to $C_{20}$ hydrocarbon group, a heteroatom containing group having up to twenty carbon atoms, silicon, germanium, tin, lead, or phosphorous;

$R^3$ is a hydrocarbon group, hydrogen, halogen, or heteroatom containing group;

$R^4$ and $R^5$ are independently an alkyl group, aryl group, substituted aryl group, cyclic alkyl group, substituted cyclic alkyl group, cyclic arylalkyl group, substituted cyclic arylalkyl group or multiple ring system;

$R^6$ and $R^7$ are independently an alkyl group, hydrogen, halogen, heteroatom, or hydrocarbyl group; and R* is a Group 14 atom containing group, hydrogen, halogen, or heteroatom containing group.

Furthermore, a method for synthesizing a pentafluorophenoxy containing catalyst composition is provided. In one aspect, the method comprises adding a catalyst composition represented by the formula:

wherein M is a metal;

X is a halogenated aryloxy group;

β and γ are groups that each comprise at least one Group 15 atom;

α is a linking moiety that forms a chemical bond to each of β and γ; and a, b, g, and n are each integers from 1 to 4; and adding a sufficient amount of a trimethylsilyl derivative comprising at least one pentafluorophenoxy group to form a metal complex comprising the at least one pentafluorophenoxy group.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Figure 1:
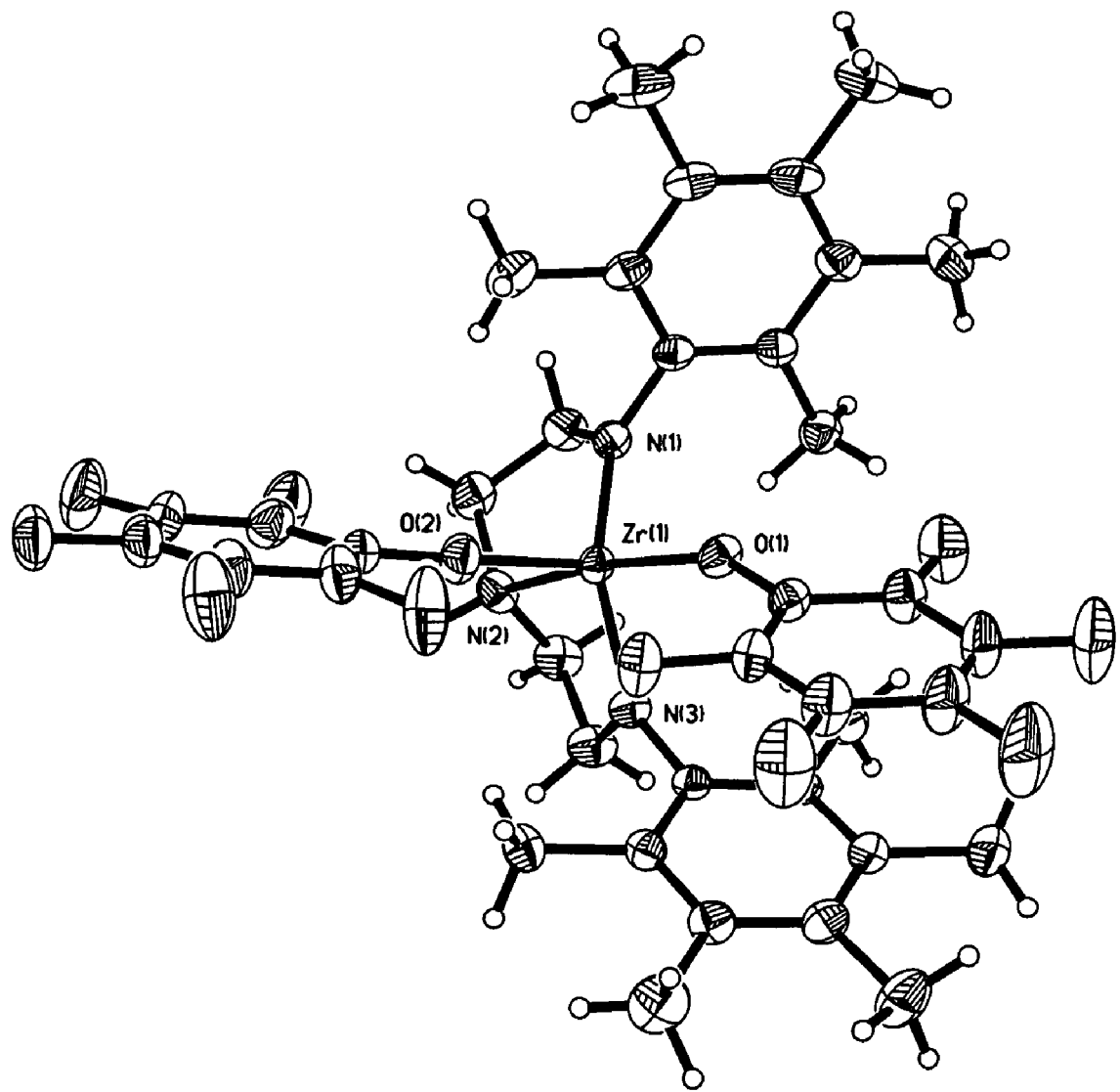
FIG. 1 shows a perspective drawing of the solid-state structure for a [(C$_6$Me$_5$)NCH$_2$CH$_2$NHCH$_2$CH$_2$N(C$_6$Me$_5$)]Zr (OC$_6$F$_5$)$_2$ molecule. Non-hydrogen atoms are represented by 30% probability thermal vibration ellipsoids and hydrogen atoms are represented by arbitrarily-small spheres which are in no way representative of their true thermal motion.

In one aspect, a non-metallocene catalyst for olefin polymerization having improved activity, solubility and reaction kinetics is provided. In another aspect, a mixed catalyst system for olefin polymerization that includes the non-metallocene catalyst is also provided. The mixed catalyst system may further include at least one metallocene catalyst. Each catalyst component of the mixed catalyst system, i.e. the non-metallocene catalyst component and the metallocene catalyst component, has essentially the same rate of decay, improving catalyst kinetics of the mixed catalyst system and overall product yield. The term "catalyst" is used interchangeably with the term "catalyst component", and includes any compound or component, or combination of compounds or components, that is capable of increasing the rate of a chemical reaction, such as the polymerization or oligomerization of one or more olefins. The term "catalyst system" may include any number of catalysts in any combination as described herein, as well as any activator in any combination as described herein. As used herein, in reference to Periodic Table "Groups" of Elements, the "new" numbering scheme for the Periodic Table Groups are used as in the CRC HANDBOOK OF CHEMISTRY AND PHYSICS (David R. Lide ed., CRC Press 81$^{st}$ ed. 2000).

Non-metallocene Catalyst

The non-metallocene catalyst is preferably a Group 15-containing catalyst. "Group 15-containing catalysts", as referred to herein, include Group 3 to Group 12 metal complexes, wherein the metal is 2 to 4 coordinate and the coordinating moiety or moieties include at least two Group 15 atoms, and up to four Group 15 atoms. In one embodiment, the Group 15-containing catalyst is a complex of a Group 4 metal and from one to four ligands such that the Group 4 metal is at least 2 coordinate and the coordinating moiety or moieties include at least two nitrogens.

In one embodiment, the Group 15-containing catalyst may include Group 4 imino-phenol complexes, Group 4 bis(amide) complexes, and Group 4 pyridyl-amide complexes that are active towards olefin polymerization to any extent. In another embodiment, the Group 15-containing catalyst may be described by the following formula (I):

$$\alpha_a\beta_b\gamma_g MX_n \qquad (I)$$

Each X in formula (I) is independently selected from halogen ions, hydrides, C1 to C12 alkyls, C2 to C12 alkenyls, C6 to C12 aryls, C7 to C20 alkylaryls, C1 to C12 alkoxys, C6 to C16 aryloxys, C7 to C18 alkylaryloxys, halogenated C1 to C12 alkyls, halogenated C2 to C12 alkenyls, halogenated C6 to C12 aryls, halogenated C7 to C20 alkylaryls, halogenated C1 to C12 alkoxys, halogenated C6 to C16 aryloxys, halogenated C7 to C18 alkylaryloxys, C1 to C12 heteroatom-containing hydrocarbons, and substituted derivatives thereof. Each X may also be selected from halogen substituted alkoxides, phenoxides, carboxylates, sulfonates, teflates, sulfides, and derivates thereof. Exemplary carboxylates includes, but are not limited to, trifluoroacetate and pentafluorobenzoate. Exemplary sulfonates include, but are not limited to, trifluoromethanesulfonate ("triflate") and benzene sulfonate. Further, each X may also be selected from fluorinated alkyl amides, fluorinated alkenyl amides, fluorinated alkylaryl amides, fluorinated alkoxy amides, fluorinated aryloxy amides, fluorinated alkylaryloxys amides, fluorinated amides, and derivates thereof. Preferably, at least one X is a halogentated aryloxy group or a derivative thereof. More preferably, at least one X is a pentafluorophenoxy group.

M is selected from Group 3 to Group 12 atoms in one embodiment; and selected from Group 3 to Group 10 atoms in a more particular embodiment; and selected from Group 3 to Group 6 atoms in yet a more particular embodiment; and selected from Ni, Cr, Ti, Zr and Hf in yet a more particular embodiment; and selected from Zr and Hf in yet a more particular embodiment.

Each β and γ are groups that each comprise at least one Group 14 to Group 16 atom; and β (when present) and γ are groups bonded to M through between 2 and 6 Group 14 to Group 16 atoms, at least two atoms being Group 15-containing atoms.

More particularly, β and γ are groups selected from Group 14 and Group 15-containing: alkyls, aryls, alkylaryls, and heterocyclic hydrocarbons, and chemically bonded combinations thereof in one embodiment; and selected from Group 14 and Group 15-containing: C$_1$ to C$_{10}$ alkyls, C$_6$ to C$_{12}$ aryls, C$_6$ to C$_{18}$ alkylaryls, and C$_4$ to C$_{12}$ heterocyclic hydrocarbons, and chemically bonded combinations thereof in a more particular embodiment; and selected from C$_1$ to C$_{10}$ alkylamines, C$_1$ to C$_{10}$ alkoxys, C$_6$ to C$_{20}$ alkylarylamines, C$_6$ to C$_{18}$ alkylaryloxys, and C$_4$ to C$_{12}$ nitrogen containing heterocyclic hydrocarbons, and C$_4$ to C$_{12}$ alkyl substituted nitrogen containing heterocyclic hydrocarbons and chemically bonded combinations thereof in yet a more particular embodiment; and selected from anilinyls, pyridyls, quinolyls, pyrrolyls, pyrimidyls, purinyls, imidazyls, indolyls, C$_1$ to C$_6$ alkyl substituted groups selected from anilinyls, pyridyls, quinolyls, pyrrolyls, pyrimidyls, purinyls, imidazyls, indolyls; C$_1$ to C$_6$ alkylamine substituted groups selected from anilinyls, pyridyls, quinolyls, pyrrolyls, pyrimidyls, purinyls, imidazyls, indolyls, amine substituted anilinyls, pyridyls, quinolyls, pyrrolyls, pyrimidyls, purinyls, imidazyls, and indolyls; hydroxy substituted groups selected from anilinyls, pyridyls, quinolyls, pyrrolyls, pyrimidyls, purinyls, imidazyls, and indolyls; methyl-substituted phenylamines, and chemically bonded combinations thereof in yet a more particular embodiment;

Each α is a linking (or "bridging") moiety that, when present, forms a chemical bond to each of β and γ, or two γ's, thus forming a "γαγ" or "γαβ" ligand bound to M; a may also comprise a Group 14 to Group 16 atom which may be bonded to M through the Group 14 to Group 16 atom in one embodiment; and more particularly, a is a divalent bridging group selected from alkylenes, arylenes, alkenylenes, heterocyclic arylenes, alkylarylenes, heteroatom containing alkylenes, heteroatom containing alkenylenes and heterocyclic hydrocarbonylenes in one embodiment; and selected from $C_1$ to $C_{10}$ alkylenes, $C_2$ to $C_{10}$ alkenylenes, $C_6$ to $C_{12}$ arylenes, $C_1$ to $C_{10}$ divalent ethers, $C_6$ to $C_{12}$ O- or N-containing arylenes, $C_2$ to $C_{10}$ alkyleneamines, $C_6$ to $C_{12}$ aryleneamines, and substituted derivatives thereof in yet a more particular embodiment;

a is an integer from 0 to 2; a is either 0 or 1 in a more particular embodiment; and a is 1 in yet a more particular embodiment; b is an integer from 0 to 2; g is an integer from 1 to 2; wherein in one embodiment, a is 1, b is 0 and g is 2; and n is an integer from 0 to 4 in one embodiment; and an integer from 1 to 3 in a more particular embodiment; and an integer from 2 to 3 in yet a more particular embodiment.

As used herein, "chemically bonded combinations thereof" means that adjacent groups, (β and γ groups) may form a chemical bond between them. In one embodiment, the β and γ groups are chemically bonded through one or more α groups there between.

As used herein, the terms "alkyleneamines" and "aryleneamines" describe alkylamines and arylamines (respectively) that are deficient by two hydrogens, thus forming chemical bonds with two adjacent γ groups, or adjacent β and γ groups. Thus, an example of an alkyleneamine is —$CH_2CH_2N(CH_3)CH_2CH_2$—, and an example of a heterocyclic hydrocarbylene or arylene amine is —$C_5H_3N$-(divalent pyridine). An "alkylene-arylamine" is a group such as, for example, —$CH_2CH_2(C_5H_3N)CH_2CH_2$—.

In another embodiment, the Group 15-containing catalyst may be represented by the structures (II) and (III):

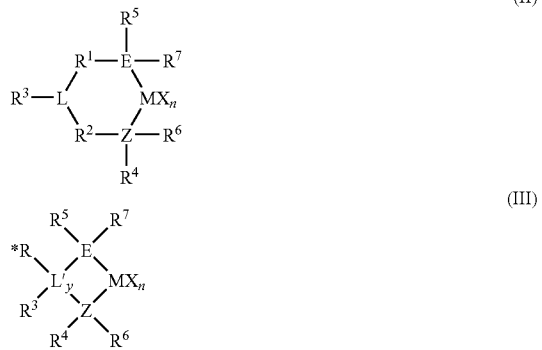

Each X in formulas (II) and (III) is independently selected from halogen ions, hydrides, C1 to C12 alkyls, C2 to C12 alkenyls, C6 to C12 aryls, C7 to C20 alkylaryls, C1 to C12 alkoxys, C6 to C16 aryloxys, C7 to C18 alkylaryloxys, halogenated C1 to C12 alkyls, halogenated C2 to C12 alkenyls, halogenated C6 to C12 aryls, halogenated C7 to C20 alkylaryls, halogenated C1 to C12 alkoxys, halogenated C6 to C16 aryloxys, halogenated C7 to C18 alkylaryloxys, C1 to C12 heteroatom-containing hydrocarbons, and substituted derivatives thereof. Each X may also be selected from halogen substituted alkoxides, phenoxides, carboxylates, sulfonates, teflates, sulfides, and derivates thereof. Exemplary carboxylates includes, but are not limited to, trifluoroacetate and pentafluorobenzoate. Exemplary sulfonates include, but are not limited to, trifluoromethanesulfonate ("triflate") and benzene sulfonate. Further, each X may also be selected from fluorinated alkyl amides, fluorinated alkenyl amides, fluorinated alkylaryl amides, fluorinated alkoxy amides, fluorinated aryloxy amides, fluorinated alkylaryloxys amides, fluorinated amides, and derivates thereof. Preferably, at least one X is a halogentated aryloxy group or a derivative thereof. More preferably, at least one X is a pentafluorophenoxy group.

E and Z are Group 15 elements independently selected from nitrogen and phosphorus in one embodiment; and nitrogen in a more particular embodiment;

L is selected from Group 15 atoms, Group 16 atoms, Group 15-containing hydrocarbylenes and a Group 16 containing hydrocarbylenes in one embodiment; wherein $R^3$ is absent when L is a Group 16 atom; in yet a more particular embodiment, when $R^3$ is absent, L is selected from heterocyclic hydrocarbylenes; and in yet a more particular embodiment, L is selected from nitrogen, phosphorous, anilinyls, pyridyls, quinolyls, pyrrolyls, pyrimidyls, purinyls, imidazyls, indolyls; $C_1$ to $C_6$ alkyl substituted groups selected from anilinyls, pyridyls, quinolyls, pyrrolyls, pyrimidyls, purinyls, imidazyls, and indolyls; $C_1$ to $C_6$ alkylamine substituted groups selected from anilinyls, pyridyls, quinolyls, pyrrolyls, pyrimidyls, purinyls, imidazyls, indolyls; amine substituted anilinyls, pyridyls, quinolyls, pyrrolyls, pyrimidyls, purinyls, imidazyls, and indolyls; hydroxy substituted groups selected from anilinyls, pyridyls, quinolyls, pyrrolyls, pyrimidyls, purinyls, imidazyls, and indolyls; methyl-substituted phenylamines, substituted derivatives thereof, and chemically bonded combinations thereof;

L' is selected from Group 15 atoms, Group 16 atoms, and Group 14 atoms in one embodiment; and selected from Group 15 and Group 16 atoms in a more particular embodiment; and is selected from groups as defined by L above in yet a more particular embodiment, wherein "EZL" and "EZL'" may be referred to as a "ligand", the EZL and EZL' ligands comprising the $R^*$ and $R^1$-$R^7$ groups;

L and L' may or may not form a bond with M;

y is an integer ranging from 0 to 2 (when y is 0, group L', *R and $R^3$ are absent);

M is selected from Group 3 to Group 5 atoms, Group 4 atoms in a more particular embodiment, and selected from Zr and Hf in yet a more particular embodiment;

n is an integer ranging from 1 to 4 in one embodiment; n is an integer ranging from 2 to 3 in a more particular embodiment;

$R^1$ and $R^2$ are independently: divalent bridging groups selected from alkylenes, arylenes, heteroatom containing alkylenes, heteroatom containing arylenes, substituted alkylenes, substituted arylenes and substituted heteroatom containing alkylenes, wherein the heteroatom is selected from silicon, oxygen, nitrogen, germanium, phosphorous, boron and sulfur in one embodiment; selected from $C_1$ to $C_{20}$ alkylenes, $C_6$ to $C_{12}$ arylenes, heteroatom-containing $C_1$ to $C_{20}$ alkylenes and heteroatom-containing $C_6$ to $C_{12}$ arylenes in a more particular embodiment; and in yet a more particular embodiment selected from —$CH_2$—, —$C(CH_3)_2$—, —$C(C_6H_5)_2$—, —$CH_2CH_2$—, —$CH_2CH_2CH_2$—, —Si$(CH_3)_2$—, —Si$(C_6H_5)_2$—, —$C_6H_{10}$—, —$C_6H_4$—, and substituted derivatives thereof, the substitutions including $C_1$ to $C_4$ alkyls, phenyl, and halogen radicals;

$R^3$ is absent in one embodiment; a group selected from hydrocarbyl groups, hydrogen radical, halogen radicals, and heteroatom-containing groups in a more particular embodiment; and selected from linear alkyls, cyclic alkyls, and branched alkyls having 1 to 20 carbon atoms in yet a more particular embodiment;

*R is absent in one embodiment; a group selected from hydrogen radical, Group 14 atom containing groups, halogen radicals, and a heteroatom-containing groups in yet a more particular embodiment;

$R^4$ and $R^5$ are independently: groups selected from alkyls, aryls, substituted aryls, cyclic alkyls, substituted cyclic alkyls, cyclic arylalkyls, substituted cyclic arylalkyls and multiple ring systems in one embodiment, each group having up to 20 carbon atoms, and between 3 and 10 carbon atoms in a more particular embodiment; selected from $C_1$ to $C_{20}$ alkyls, $C_1$ to $C_{20}$ aryls, $C_1$ to $C_{20}$ arylalkyls, and heteroatom-containing groups (for example $PR_3$, where R is an alkyl group) in yet a more particular embodiment; and $R^6$ and $R^7$ are independently: absent in one embodiment; groups selected from hydrogen radicals, halogen radicals, heteroatom-containing groups and hydrocarbyls in a more particular embodiment; selected from linear, cyclic and branched alkyls having from 1 to 20 carbon atoms in yet a more particular embodiment;

$R^1$ and $R^2$ may be associated with one another, and/or $R^4$ and $R^5$ may be associated with one another as through a chemical bond.

In yet another embodiment, the Group 15-containing catalyst may be represented by the structures (IV), (V) and (VI) (where "N" is nitrogen):

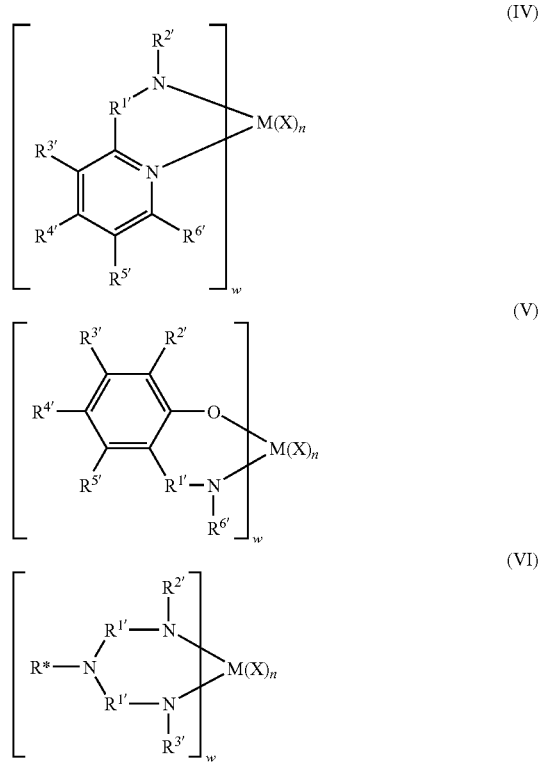

The structure (IV) represents pyridyl-amide structures, the structure (V) represents imino-phenol structures, and the structure (VI) represents bis(amide) structures. Each X in formulas (IV-VI) is independently selected from halogen ions, hydrides, C1 to C12 alkyls, C2 to C12 alkenyls, C6 to C12 aryls, C7 to C20 alkylaryls, C1 to C12 alkoxys, C6 to C16 aryloxys, C7 to C18 alkylaryloxys, halogenated C1 to C12 alkyls, halogenated C2 to C12 alkenyls, halogenated C6 to C12 aryls, halogenated C7 to C20 alkylaryls, halogenated C1 to C12 alkoxys, halogenated C6 to C16 aryloxys, halogenated C7 to C18 alkylaryloxys, C1 to C12 heteroatom-containing hydrocarbons, and substituted derivatives thereof. Each X may also be selected from halogen substituted alkoxides, phenoxides, carboxylates, sulfonates, teflates, sulfides, and derivates thereof. Exemplary carboxylates includes, but are not limited to, trifluoroacetate and pentafluorobenzoate. Exemplary sulfonates include, but are not limited to, trifluoromethanesulfonate ("triflate") and benzene sulfonate. Further, each X may also be selected from fluorinated alkyl amides, fluorinated alkenyl amides, fluorinated alkylaryl amides, fluorinated alkoxy amides, fluorinated aryloxy amides, fluorinated alkylaryloxys amides, fluorinated amides, and derivates thereof. Preferably, at least one X is a halogentated aryloxy group or a derivative thereof. More preferably, at least one X is a pentafluorophenoxy group.

w is an integer from 1 to 3, and 1 or 2 in a more particular embodiment, and 1 in yet a more particular embodiment; M is a Group 3 to Group 13 element, a Group 3 to Group 6 element in a more particular embodiment, and a Group 4 element in yet a more particular embodiment; and n is an integer ranging from 0 to 4, and from 1 to 3 in a more particular embodiment, and from 2 to 3 in yet a more particular embodiment, and 2 in yet a more particular embodiment.

In structures (IV), (V), and (VI), $R^{1'}$ is selected from hydrocarbylenes and heteroatom-containing hydrocarbylenes in one embodiment, and selected from $—SiR_2—$, alkylenes, arylenes, alkenylenes and substituted alkylenes, substituted alkenylenes and substituted arylenes in another embodiment; and selected from $—SiR_2—$, $C_1$ to $C_6$ alkylenes, $C_6$ to $C_{12}$ arylenes, $C_1$ to $C_6$ substituted alkylenes and $C_6$ to $C_{12}$ substituted arylenes in another embodiment.

R is selected from $C_1$ to $C_6$ alkyls and $C_6$ to $C_{12}$ aryls; and $R^{2'}$, $R^{3'}$, $R^{4'}$, $R^{5'}$, $R^{6'}$ and R* are independently selected from hydride, $C_1$ to $C_{10}$ alkyls, $C_6$ to $C_{12}$ aryls, $C_6$ to $C_{18}$ alkylaryls, $C_4$ to $C_{12}$ heterocyclic hydrocarbyls, substituted $C_1$ to $C_{10}$ alkyls, substituted $C_6$ to $C_{12}$ aryls, substituted $C_6$ to $C_{18}$ alkylaryls, and substituted $C_4$ to $C_{12}$ heterocyclic hydrocarbyls and chemically bonded combinations thereof in one embodiment.

R* is absent in a particular embodiment; and in another embodiment, R*-N represents a nitrogen containing group or ring such as a pyridyl group or a substituted pyridyl group that is bridged by the $R^{1'}$ groups. In yet another embodiment, R*-N is absent, and the $R^{1'}$ groups form a chemical bond to one another.

In one embodiment of structures (IV), (V), and (VI), $R^{1'}$ is selected from methylene, ethylene, 1-propylene, 2-propylene, $=Si(CH_3)_2$, $=Si(phenyl)_2$, $—CH=$, $—C(CH_3)=$, $—C(phenyl)_2—$, $—C(phenyl)=$ (wherein "=" represents two chemical bonds), and the like.

In a particular embodiment of structure (V), $R^{2'}$ and $R^{4'}$ are selected from 2-methylphenyl, 2-n-propylphenyl, 2-iso-propylphenyl, 2-iso-butylphenyl, 2-tert-butylphenyl, 2-fluorophenyl, 2-chlorophenyl, 2-bromophenyl, 2-methyl-4-chlorophenyl, 2-n-propyl-4-chlorophenyl, 2-iso-propyl-4-chlorophenyl, 2-iso-butyl-4-chlorophenyl, 2-tert-butyl-4-chlorophenyl, 2-methyl-4-fluorophenyl, 2-n-propyl-4-fluorophenyl, 2-iso-propyl-4-fluorophenyl, 2-iso-butyl-4-fluorophenyl, 2-tert-butyl-4-fluorophenyl, 2-methyl-4- bromophenyl, 2-n-propyl-4-bromophenyl, 2-iso-propyl-4-bromophenyl, 2-iso-butyl-4-bromophenyl, 2-tert-butyl-4-bromophenyl, and the like.

In yet another particular embodiment of structures (IV) and (VI), $R^{2'}$ and $R^{3'}$ are selected from 2-methylphenyl, 2-n-propylphenyl, 2-iso-propylphenyl, 2-iso-butylphenyl, 2-tert-butylphenyl, 2-fluorophenyl, 2-chlorophenyl, 2-bromophenyl, 4-methylphenyl, 4-n-propylphenyl, 4-iso-propylphenyl, 4-iso-butylphenyl, 4-tert-butylphenyl, 4-fluorophenyl, 4-chlorophenyl, 4-bromophenyl, 6-methylphenyl, 6-n-propylphenyl, 6-iso-propylphenyl, 6-iso-butylphenyl, 6-tert-butylphenyl, 6-fluorophenyl, 6-chlorophenyl, 6-bromophenyl, 2,6-dimethylphenyl, 2,6-di-n-propylphenyl, 2,6-di-iso-propylphenyl, 2,6-di-isobutylphenyl, 2,6-di-tert-butylphenyl, 2,6-difluorophenyl, 2,6-dichlorophenyl, 2,6-dibromophenyl, 2,4,6-trimethylphenyl, 2,4,6-tri-n-propylphenyl, 2,4,6-tri-iso-propylphenyl, 2,4,6-tri-iso-butylphenyl, 2,4,6-tri-tert-butylphenyl, 2,4,6-trifluorophenyl, 2,4,6-trichlorophenyl, 2,4,6-tribromophenyl, 2,3,4,5,6-pentafluorophenyl, 2,3,4,5,6-pentachlorophenyl, 2,3,4,5,6-pentabromophenyl, and the like.

As used here, "chemically bonded combinations" means that adjacent groups may form a chemical bond between them, thus forming a ring system, either saturated, partially unsaturated, or aromatic.

In still yet another embodiment, the Group 15-containing catalyst may be represented by the structures (VIIa)-(VIIf) (where "N" is nitrogen):

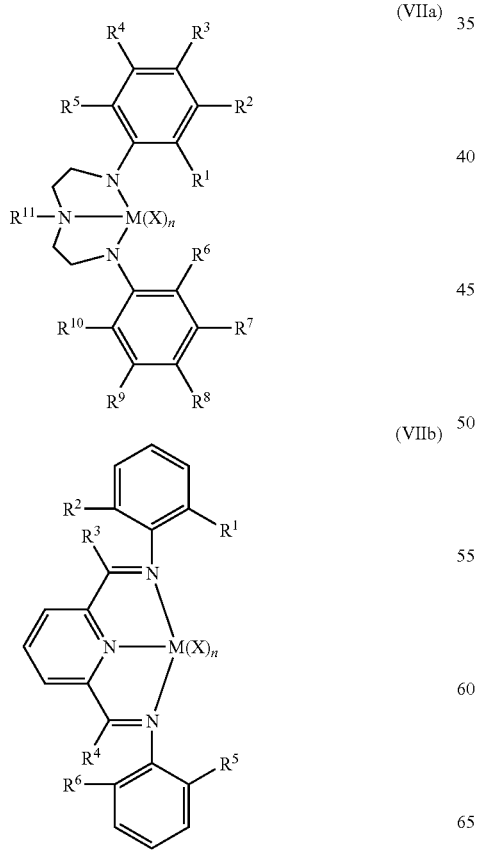

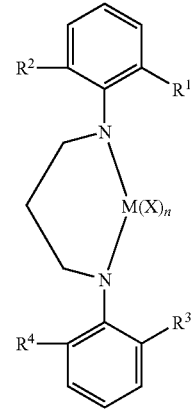

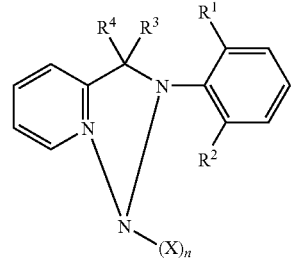

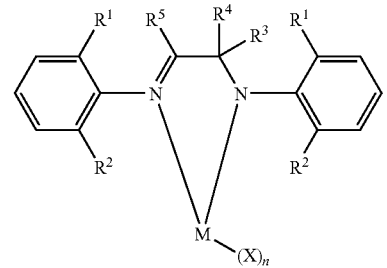

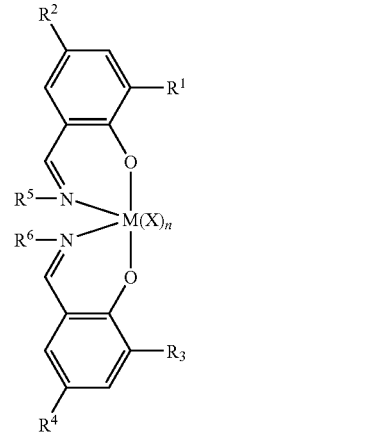

In structures (VIIa) through (VIIf) M is selected from Group 4 atoms in one embodiment; and M is selected from Zr and Hf in a more particular embodiment; n is an integer ranging from 0 to 4, and from 2 to 3 in a more particular embodiment; and $R^1$ through $R^{11}$ in structures (VIIa) through (VIIf) are selected from hydride, fluorine radical, chlorine radical, bromine radical, methyl, ethyl, n-propyl, isopropyl, n-butyl, isobutyl, tert-butyl and phenyl.

Each X in formulas (VIIa)-(VIIf) is independently selected from halogen ions, hydrides, C1 to C12 alkyls, C2 to C12 alkenyls, C6 to C12 aryls, C7 to C20 alkylaryls, C1 to C12 alkoxys, C6 to C16 aryloxys, C7 to C18 alkylaryloxys, halogenated C1 to C12 alkyls, halogenated C2 to C12 alkenyls, halogenated C6 to C12 aryls, halogenated C7 to C20 alkylaryls, halogenated C1 to C12 alkoxys, halogenated C6 to C16 aryloxys, halogenated C7 to C18 alkylaryloxys, C1 to C12 heteroatom-containing hydrocarbons, and substituted derivatives thereof. Each X may also be selected from halogen substituted alkoxides, phenoxides, carboxylates, sulfonates, teflates, sulfides, and derivates thereof. Exemplary carboxylates includes, but are not limited to, trifluoroacetate and pentafluorobenzoate. Exemplary sulfonates include, but are not limited to, trifluoromethanesulfonate ("triflate") and benzene sulfonate. Further, each X may also be selected from fluorinated alkyl amides, fluorinated alkenyl amides, fluorinated alkylaryl amides, fluorinated alkoxy amides, fluorinated aryloxy amides, fluorinated alkylaryloxys amides, fluorinated amides, and derivates thereof. Preferably, at least one X is a halogentated aryloxy group or a derivative thereof. More preferably, at least one X is a pentafluorophenoxy group.

Mixed Catalyst

The mixed catalyst system may be described as a bimetallic catalyst composition or a multi-catalyst composition. As used herein, the terms "bimetallic catalyst composition" and "bimetallic catalyst" include any composition, mixture, or system that includes two or more different catalyst components, each having a different metal group. The terms "multi-catalyst composition" and "multi-catalyst" include any composition, mixture, or system that includes two or more different catalyst components regardless of the metals. Therefore, the terms "bimetallic catalyst composition," "bimetallic catalyst," "multi-catalyst composition," and "multi-catalyst" will be collectively referred to as a "mixed catalyst system," unless specifically noted otherwise.

Metallocene Catalyst Component

As mentioned above, the mixed catalyst system includes the Group 15-containing catalyst described above and one or more metallocene catalyst components. The metallocene catalyst component may include "half sandwich" and "full sandwich" compounds having one or more Cp ligands (cyclopentadienyl and ligands isolobal to cyclopentadienyl) bound to at least one Group 3 to Group 12 metal atom, and one or more leaving group(s) bound to the at least one metal atom.

The Cp ligands are one or more rings or ring system(s), at least a portion of which includes π-bonded systems, such as cycloalkadienyl ligands and heterocyclic analogues. The ring(s) or ring system(s) typically comprise atoms selected from the group consisting of Groups 13 to 16 atoms, and more particularly, the atoms that make up the Cp ligands are selected from the group consisting of carbon, nitrogen, oxygen, silicon, sulfur, phosphorous, germanium, boron and aluminum and combinations thereof, wherein carbon makes up at least 50% of the ring members. Even more particularly, the Cp ligand(s) are selected from the group consisting of substituted and unsubstituted cyclopentadienyl ligands and ligands isolobal to cyclopentadienyl, non-limiting examples of which include cyclopentadienyl, indenyl, fluorenyl and other structures. Further non-limiting examples of such ligands include cyclopentadienyl, cyclopentaphenanthreneyl, indenyl, benzindenyl, fluorenyl, octahydrofluorenyl, cyclooctatetraenyl, cyclopentacyclododecene, phenanthrindenyl, 3,4-benzofluorenyl, 9-phenylfluorenyl, 8-H-cyclopent[a]acenaphthylenyl, 7H-dibenzofluorenyl, indeno[1, 2-9]anthrene, thiophenoindenyl, thiophenofluorenyl, hydrogenated versions thereof (e.g., 4,5,6,7-tetrahydroindenyl, or "H$_4$Ind"), substituted versions thereof (as described in more detail below), and heterocyclic versions thereof.

The metal atom "M" of the metallocene catalyst compound, may be selected from the group consisting of Groups 3 through 12 atoms and lanthanide Group atoms in one embodiment; and selected from the group consisting of Groups 3 through 10 atoms in a more particular embodiment, and selected from the group consisting of Sc, Ti, Zr, Hf, V, Nb, Ta, Mn, Re, Fe, Ru, Os, Co, Rh, Ir, and Ni in yet a more particular embodiment; and selected from the group consisting of Groups 4, 5 and 6 atoms in yet a more particular embodiment, and a Ti, Zr, Hf atoms in yet a more particular embodiment, and Zr in yet a more particular embodiment. The oxidation state of the metal atom "M" may range from 0 to +7 in one embodiment; and in a more particular embodiment, is +1, +2, +3, +4 or +5; and in yet a more particular embodiment is +2, +3 or +4.

The groups bound to the metal atom "M" are such that the compounds described below in the formulas and structures are neutral, unless otherwise indicated. The Cp ligand(s) form at least one chemical bond with the metal atom M to form the "metallocene catalyst compound." The Cp ligands are distinct from the leaving groups bound to the catalyst compound in that they are not highly susceptible to substitution/abstraction reactions.

In one aspect, the one or more metallocene catalyst components are represented by the formula (VIII):

$$Cp^A Cp^B MX_n \qquad \text{(VIII)}$$

wherein M is as described above; each X is chemically bonded to M; each Cp group is chemically bonded to M; and n is 0 or an integer from 1 to 4, and either 1 or 2 in a particular embodiment.

The ligands represented by $Cp^A$ and $Cp^B$ in formula (VIII) may be the same or different cyclopentadienyl ligands or ligands isolobal to cyclopentadienyl, either or both of which may contain heteroatoms and either or both of which may be substituted by a group R. In one embodiment, $Cp^A$ and $Cp^B$ are independently selected from the group consisting of cyclopentadienyl, indenyl, tetrahydroindenyl, fluorenyl, and substituted derivatives of each.

Independently, each $Cp^A$ and $Cp^B$ of formula (VIII) may be unsubstituted or substituted with any one or combination of substituent groups R. Non-limiting examples of substituent groups R as used in structure (II) include hydrogen radicals, alkyls, alkenyls, alkynyls, cycloalkyls, aryls, acyls, aroyls, alkoxys, aryloxys, alkylthiols, dialkylamines, alkylamidos, alkoxycarbonyls, aryloxycarbonyls, carbomoyls, alkyl- and dialkyl-carbamoyls, acyloxys, acylaminos, aroylaminos, and combinations thereof.

More particular non-limiting examples of alkyl substituents R associated with formula (II) includes methyl, ethyl, propyl, butyl, pentyl, hexyl, cyclopentyl, cyclohexyl, benzyl, phenyl, methylphenyl, and tert-butylphenyl groups and the like, including all their isomers, for example tertiary-butyl, isopropyl, and the like. Other possible radicals include substituted alkyls and aryls such as, for example, fluoromethyl, fluoroethyl, difluoroethyl, iodopropyl, bromohexyl, chlorobenzyl and hydrocarbyl substituted organometalloid radicals including trimethylsilyl, trimethylgermyl, methyldiethylsilyl and the like; and halocarbyl-substituted organometalloid radicals including tris(trifluoromethyl)silyl, methylbis(difluoromethyl)silyl, bromomethyldimethylgermyl and the like; and disubstituted boron radicals including dimethylboron for example; and disubstituted Group 15 radicals including dimethylamine, dimethylphosphine, diphenylamine, methylphenylphosphine, Group 16 radicals including methoxy, ethoxy, propoxy, phenoxy, methylsulfide and ethylsulfide. Other substituents R include olefins such as but not limited to olefinically unsaturated substituents including vinyl-terminated ligands, for example 3-butenyl, 2-propenyl, 5-hexenyl and the like. In one embodiment, at least two R groups, two adjacent R groups in one embodiment, are joined to form a ring structure having from 3 to 30 atoms selected from the group consisting of carbon, nitrogen, oxygen, phosphorous, silicon, germanium, aluminum, boron and combinations thereof. Also, a substituent group R group such as 1-butanyl may form a bonding association to the element M.

Each X in formula (VIII) is independently selected from the following: halogen ions, hydrides, $C_1$ to $C_{12}$ alkyls, $C_2$ to $C_{12}$ alkenyls, $C_6$ to $C_{12}$ aryls, $C_7$ to $C_{20}$ alkylaryls, $C_1$ to $C_{12}$ alkoxys, $C_6$ to $C_{16}$ aryloxys, $C_7$ to $C_{18}$ alkylaryloxys, $C_1$ to $C_{12}$ fluoroalkyls, $C_6$ to $C_{12}$ fluoroaryls, and $C_1$ to $C_{12}$ heteroatom-containing hydrocarbons and substituted derivatives thereof in a more particular embodiment; hydride, halogen ions, $C_1$ to $C_6$ alkyls, $C_2$ to $C_6$ alkenyls, $C_7$ to $C_{18}$ alkylaryls, $C_1$ to $C_6$ alkoxys, $C_6$ to $C_{14}$ aryloxys, $C_7$ to $C_{16}$ alkylaryloxys, $C_1$ to $C_6$ alkylcarboxylates, $C_1$ to $C_6$ fluorinated alkylcarboxylates, $C_6$ to $C_{12}$ arylcarboxylates, $C_7$ to $C_{18}$ alkylarylcarboxylates, $C_1$ to $C_6$ fluoroalkyls, $C_2$ to $C_6$ fluoroalkenyls, and $C_7$ to $C_{18}$ fluoroalkylaryls in yet a more particular embodiment; hydride, chloride, fluoride, methyl, phenyl, phenoxy, benzoxy, tosyl, fluoromethyls and fluorophenyls in yet a more particular embodiment; $C_1$ to $C_{12}$ alkyls, $C_2$ to $C_{12}$ alkenyls, $C_6$ to $C_{12}$ aryls, $C_7$ to $C_{20}$ alkylaryls, substituted $C_1$ to $C_{12}$ alkyls, substituted $C_6$ to $C_{12}$ aryls, substituted $C_7$ to $C_{20}$ alkylaryls and $C_1$ to $C_{12}$ heteroatom-containing alkyls, $C_1$ to $C_{12}$ heteroatom-containing aryls and $C_1$ to $C_{12}$ heteroatom-containing alkylaryls in yet a more particular embodiment; chloride, fluoride, $C_1$ to $C_6$ alkyls, $C_2$ to $C_6$ alkenyls, $C_7$ to $C_{18}$ alkylaryls, halogenated $C_1$ to $C_6$ alkyls, halogenated $C_2$ to $C_6$ alkenyls, and halogenated $C_7$ to $C_{18}$ alkylaryls in yet a more particular embodiment; fluoride, methyl, ethyl, propyl, phenyl, methylphenyl, dimethylphenyl, trimethylphenyl, fluoromethyls (mono-, di- and trifluoromethyls) and fluorophenyls (mono-, di-, tri-, tetra- and pentafluorophenyls) in yet a more particular embodiment.

Other non-limiting examples of X groups in formula (VIII) include amines, phosphines, ethers, carboxylates, dienes, hydrocarbon radicals having from 1 to 20 carbon atoms, fluorinated hydrocarbon radicals (e.g., —$C_6F_5$ (pentafluorophenyl)), fluorinated alkylcarboxylates (e.g., $CF_3C(O)O^-$), hydrides and halogen ions and combinations thereof. Other examples of X ligands include alkyl groups such as cyclobutyl, cyclohexyl, methyl, heptyl, tolyl, trifluoromethyl, tetramethylene, pentamethylene, methylidene, methyoxy, ethyoxy, propoxy, phenoxy, bis(N-methylanilide), dimethylamide, dimethylphosphide radicals and the like. In one embodiment, two or more X's form a part of a fused ring or ring system.

In another aspect, the metallocene catalyst component includes those of formula (VIII) where $Cp^A$ and $Cp^B$ are bridged to each other by at least one bridging group, (A), such that the structure is represented by formula (IX):

$$Cp^A(A)Cp^B MX_n \qquad (IX)$$

These bridged compounds represented by formula (IX) are known as "bridged metallocenes". $CP^A$, $CP^B$, M, X and n are as defined above for formula (VIII); and wherein each Cp ligand is chemically bonded to M, and (A) is chemically bonded to each Cp. Non-limiting examples of bridging group (A) include divalent hydrocarbon groups containing at least one Group 13 to 16 atom, such as but not limited to at least one of a carbon, oxygen, nitrogen, silicon, aluminum, boron, germanium and tin atom and combinations thereof; wherein the heteroatom may also be $C_1$ to $C_{12}$ alkyl or aryl substituted to satisfy neutral valency.

The bridging group (A) may also contain substituent groups R as defined above for formula (VIII) including halogen radicals and iron. More particular non-limiting examples of bridging group (A) are represented by $C_1$ to $C_6$ alkylenes, substituted $C_1$ to $C_6$ alkylenes, oxygen, sulfur, $R'_2C=$, $R'_2Si=$, $—Si(R')_2Si(R'_2)$, $R'_2Ge=$, $R'P=$ (wherein "=" represents two chemical bonds), where R' is independently selected from the group consisting of hydride, hydrocarbyl, substituted hydrocarbyl, halocarbyl, substituted halocarbyl, hydrocarbyl-substituted organometalloid, halocarbyl-substituted organometalloid, disubstituted boron, disubstituted Group 15 atoms, substituted Group 16 atoms, and halogen radical; and wherein two or more R' may be joined to form a ring or ring system. In one embodiment, the bridged metallocene catalyst component of formula (IX) has two or more bridging groups (A).

Other non-limiting examples of bridging group (A) include methylene, ethylene, ethylidene, propylidene, isopropylidene, diphenylmethylene, 1,2-dimethylethylene, 1,2-diphenylethylene, 1,1,2,2-tetramethylethylene, dimethylsilyl, diethylsilyl, methyl-ethylsilyl, trifluoromethylbutylsilyl, bis(trifluoromethyl)silyl, di(n-butyl)silyl, di(n-propyl)silyl, di(i-propyl)silyl, di(n-hexyl)silyl, dicyclohexylsilyl, diphenylsilyl, cyclohexylphenylsilyl, t-butylcyclohexylsilyl, di(t-butylphenyl)silyl, di(p-tolyl)silyl and the corresponding moieties wherein the Si atom is replaced by a Ge or a C atom; dimethylsilyl, diethylsilyl, dimethylgermyl and diethylgermyl.

In another embodiment, bridging group (A) may also be cyclic, comprising, for example 4 to 10, 5 to 7 ring members in a more particular embodiment. The ring members may be selected from the elements mentioned above, from one or more of B, C, Si, Ge, N and O in a particular embodiment. Non-limiting examples of ring structures which may be present as or part of the bridging moiety are cyclobutylidene, cyclopentylidene, cyclohexylidene, cycloheptylidene, cyclooctylidene and the corresponding rings where one or two carbon atoms are replaced by at least one of Si, Ge, N and O, in particular, Si and Ge. The bonding arrangement between the ring and the Cp groups may be either cis-, trans-, or a combination.

The cyclic bridging groups (A) may be saturated or unsaturated and/or carry one or more substituents and/or be fused to one or more other ring structures. If present, the one or more substituents are selected from the group consisting of hydrocarbyl (e.g., alkyl such as methyl) and halogen (e.g., F, Cl) in one embodiment. The one or more Cp groups which the above cyclic bridging moieties may optionally be fused to may be saturated or unsaturated and are selected from the group consisting of those having 4 to 10, more particularly 5, 6 or 7 ring members (selected from the group consisting of C, N, O and S in a particular embodiment) such as, for example, cyclopentyl, cyclohexyl and phenyl. Moreover, these ring structures may themselves be fused such as, for example, in the case of a naphthyl group. Moreover, these (optionally fused) ring structures may carry one or more substituents. Illustrative, non-limiting examples of these substituents are hydrocarbyl (particularly alkyl) groups and halogen atoms.

The ligands $Cp^A$ and $Cp^B$ of formula (VIII) and (IX) are different from each other in one embodiment, and the same in another embodiment.

In yet another aspect, the metallocene catalyst components include mono-ligand metallocene compounds (e.g., mono cyclopentadienyl catalyst components) such as described in WO 93/08221 for example. In this embodiment, the at least one metallocene catalyst component is a bridged "half-sandwich" metallocene represented by the formula (X):

$$Cp^A(A)QMX_n \qquad (X)$$

wherein $Cp^A$ is defined above with reference to formula (VIII) and is bound to M; (A) is a bridging group bonded to Q and $Cp^A$; and wherein an atom from the Q group is bonded to M; and n is 0 or an integer from 1 to 3; 1 or 2 in a particular embodiment. In formula (X), $Cp^A$, (A) and Q may form a fused ring system. The X groups and n of formula (X) are as defined above in formula (VIII) and (IX). In one embodiment, $Cp^A$ is selected from the group consisting of cyclopentadienyl, indenyl, tetrahydroindenyl, fluorenyl, substituted versions thereof, and combinations thereof.

In formula (X), Q is a heteroatom-containing ligand in which the bonding atom (the atom that is bonded with the metal M) is selected from the group consisting of Group 15 atoms and Group 16 atoms in one embodiment, and selected from the group consisting of nitrogen, phosphorus, oxygen or sulfur atom in a more particular embodiment, and nitrogen and oxygen in yet a more particular embodiment. Non-limiting examples of Q groups include alkylamines, arylamines, mercapto compounds, ethoxy compounds, carboxylates (e.g., pivalate), carbamates, azenyl, azulene, pentalene, phosphoyl, phosphinimine, pyrrolyl, pyrozolyl, carbazolyl, borabenzene other compounds comprising Group 15 and Group 16 atoms capable of bonding with M.

In yet another aspect, the at least one metallocene catalyst component is an unbridged "half sandwich" metallocene represented by the formula (XI):

$$Cp^A MQ_q X_n \qquad (XI)$$

wherein $Cp^A$ is defined as for the Cp groups in (VIII) and is a ligand that is bonded to M; each Q is independently bonded to M; Q is also bound to $Cp^A$ in one embodiment; X is a leaving group as described above in (VIII); n ranges from 0 to 3, and is 1 or 2 in one embodiment; q ranges from 0 to 3, and is 1 or 2 in one embodiment. In one embodiment, $Cp^A$ is selected from the group consisting of cyclopentadienyl, indenyl, tetrahydroindenyl, fluorenyl, substituted version thereof, and combinations thereof.

In formula (XII), Q is selected from the group consisting of $ROO^-$, $RO—$, $R(O)—$, $—NR—$, $—CR_2—$, $—S—$, $—NR_2$, $—CR_3$, $—SR$, $—SiR_3$, $—PR_2$, $—H$, and substituted and unsubstituted aryl groups, wherein R is selected from the group consisting of $C_1$ to $C_6$ alkyls, $C_6$ to $C_{12}$ aryls, $C_1$ to $C_6$ alkylamines, $C_6$ to $C_{12}$ alkylarylamines, $C_1$ to $C_6$ alkoxys, $C_6$ to $C_{12}$ aryloxys, and the like. Non-limiting examples of Q include $C_1$ to $C_{12}$ carbamates, $C_1$ to $C_{12}$ carboxylates (e.g., pivalate), $C_2$ to $C_{20}$ alkyls, and $C_2$ to $C_{20}$ heteroallyl moieties.

Described another way, the "half sandwich" metallocenes above can be described as in for example, U.S. Pat. No. 6,069,213:

$$Cp^A M(Q_2GZ)X_n \text{ or } T(Cp^A M(Q_2GZ)X_n)_m \qquad (XII)$$

wherein M, $Cp^A$, X and n are as defined above;

$Q_2GZ$ forms a polydentate ligand unit (e.g., pivalate), wherein at least one of the Q groups form a bond with M, and is defined such that each Q is independently selected from the group consisting of $—O—$, $—NR—$, $—CR_2—$ and $—S—$; G is either carbon or silicon; and Z is selected from the group consisting of R, $—OR$, $—NR_2$, $—CR_3$, $—SR$, $—SiR_3$, $—PR_2$, and hydride, providing that when Q is $—NR—$, then Z is selected from the group consisting of $—OR$, $—NR_2$, $—SR$, $—SiR_3$, $—PR_2$; and provided that neutral valency for Q is satisfied by Z; and wherein each R is independently selected from the group consisting of $C_1$ to $C_{10}$ heteroatom containing groups, $C_1$ to $C_{10}$ alkyls, $C_6$ to $C_{12}$ aryls, $C_6$ to $C_{12}$ alkylaryls, $C_1$ to $C_{10}$ alkoxys, and $C_6$ to $C_{12}$ aryloxys;

n is 1 or 2 in a particular embodiment; and

T is a bridging group selected from the group consisting of $C_1$ to $C_{10}$ alkylenes, $C_6$ to $C_{12}$ arylenes and $C_1$ to $C_{10}$ heteroatom containing groups, and $C_6$ to $C_{12}$ heterocyclic groups; wherein each T group bridges adjacent "$Cp^A M(Q_2GZ)X_n$" groups, and is chemically bonded to the $Cp^A$ groups.

m is an integer from 1 to 7; m is an integer from 2 to 6 in a more particular embodiment.

In another aspect, the at least one metallocene catalyst component can be described more particularly in structures (XIIIa), (XIIIb), (XIIIc), (XIIId), (XIIIe), and (XIIIf):

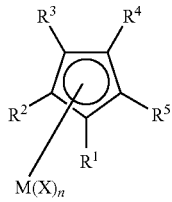

(XIIIa-ii)

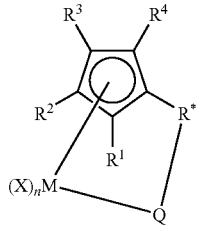

(XIIIa-i)

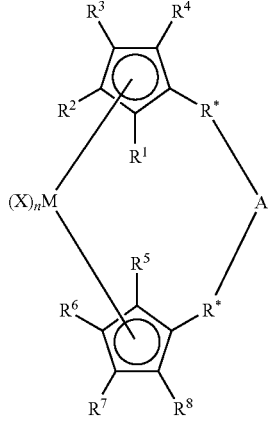

(XIIIb)

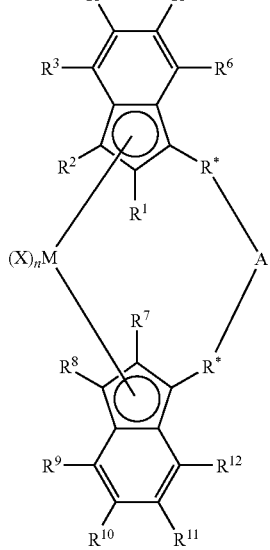

(XIIIc)

-continued

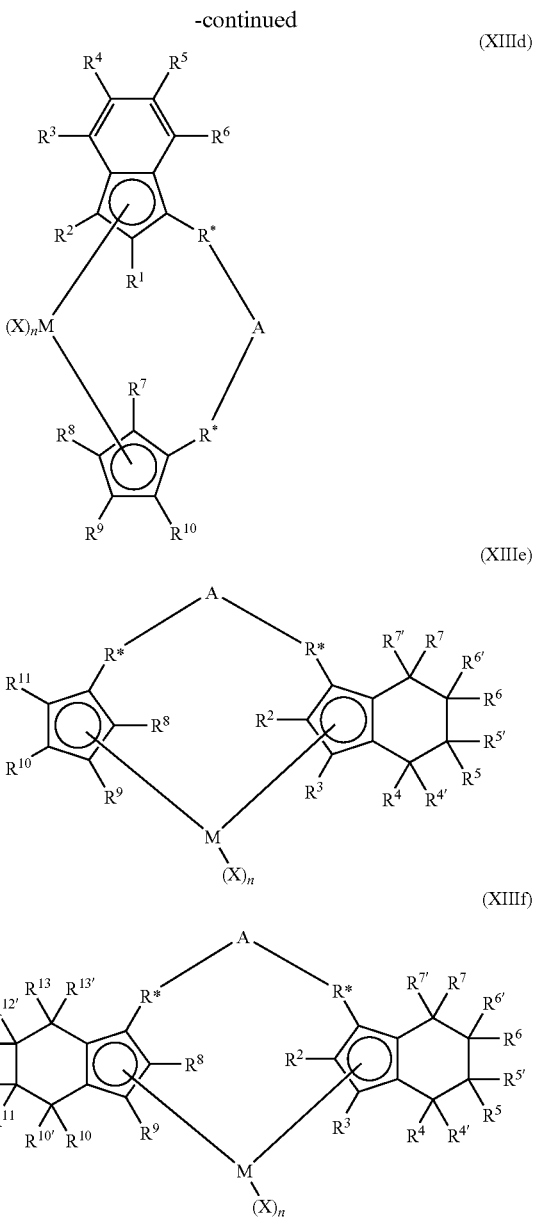

(XIIId)

(XIIIe)

(XIIIf)

wherein in structures (XIIIa) to (XIIIf), M is selected from the group consisting of Group 3 to Group 12 atoms, and selected from the group consisting of Group 3 to Group 10 atoms in a more particular embodiment, and selected from the group consisting of Group 3 to Group 6 atoms in yet a more particular embodiment, and selected from the group consisting of Group 4 atoms in yet a more particular embodiment, and selected from the group consisting of Zr and Hf in yet a more particular embodiment; and is Zr in yet a more particular embodiment;

wherein Q in (XIIIa) to (XIIIf) is selected from the group consisting of alkylenes, aryls, arylenes, alkoxys, aryloxys, amines, arylamines (e.g., pyridyl) alkylamines, phosphines, alkylphosphines, substituted alkyls, substituted aryls, substituted alkoxys, substituted aryloxys, substituted amines, substituted alkylamines, substituted phosphines, substituted alkylphosphines, carbamates, heteroallyls, carboxylates (non-limiting examples of suitable carbamates and carboxylates include trimethylacetate, trimethylacetate, methylacetate, p-toluate, benzoate, diethylcarbamate, and dimethylcarbamate), fluorinated alkyls, fluorinated aryls, and fluorinated alkylcarboxylates; wherein the saturated groups defining Q comprise from 1 to 20 carbon atoms in one embodiment; and wherein the aromatic groups comprise from 5 to 20 carbon atoms in one embodiment;

wherein each R* is independently: selected from the group consisting of hydrocarbylenes and heteroatom-containing hydrocarbylenes in one embodiment; and selected from the group consisting of alkylenes, substituted alkylenes and heteroatom-containing hydrocarbylenes in another embodiment; and selected from the group consisting of $C_1$ to $C_{12}$ alkylenes, $C_1$ to $C_{12}$ substituted alkylenes, and $C_1$ to $C_{12}$ heteroatom-containing hydrocarbylenes in a more particular embodiment; and selected from the group consisting of $C_1$ to $C_4$ alkylenes in yet a more particular embodiment; and wherein both R* groups are identical in another embodiment in structures (XIIIf);

A is as described above for (A) in structure (IX), and more particularly, selected from the group consisting of a chemical bond, —O—, —S—, —SO$_2$—, —NR—, =SiR$_2$, =GeR$_2$, =SnR$_2$, —R$_2$SiSiR$_2$—, RP=, $C_1$ to $C_{12}$ alkylenes, substituted $C_1$ to $C_{12}$ alkylenes, divalent $C_4$ to $C_{12}$ cyclic hydrocarbons and substituted and unsubstituted aryl groups in one embodiment; and selected from the group consisting of $C_5$ to $C_8$ cyclic hydrocarbons, —CH$_2$CH$_2$—, =CR$_2$ and =SiR$_2$ in a more particular embodiment; wherein and R is selected from the group consisting of alkyls, cycloalkyls, aryls, alkoxys, fluoroalkyls and heteroatom-containing hydrocarbons in one embodiment; and R is selected from the group consisting of $C_1$ to $C_6$ alkyls, substituted phenyls, phenyl, and $C_1$ to $C_6$ alkoxys in a more particular embodiment; and R is selected from the group consisting of methoxy, methyl, phenoxy, and phenyl in yet a more particular embodiment;

wherein A may be absent in yet another embodiment, in which case each R* is defined as for $R^1$-$R^{13}$;

each X is as described above in (VIII);

n is an integer from 0 to 4, and from 1 to 3 in another embodiment, and 1 or 2 in yet another embodiment; and $R^1$ through $R^{13}$ are independently: selected from the group consisting of hydrogen radical, halogen radicals, $C_1$ to $C_{12}$ alkyls, $C_2$ to $C_{12}$ alkenyls, $C_6$ to $C_{12}$ aryls, $C_7$ to $C_{20}$ alkylaryls, $C_1$ to $C_{12}$ alkoxys, $C_1$ to $C_{12}$ fluoroalkyls, $C_6$ to $C_{12}$ fluoroaryls, and $C_1$ to $C_{12}$ heteroatom-containing hydrocarbons and substituted derivatives thereof in one embodiment; selected from the group consisting of hydrogen radical, fluorine radical, chlorine radical, bromine radical, $C_1$ to $C_6$ alkyls, $C_2$ to $C_6$ alkenyls, $C_7$ to $C_{18}$ alkylaryls, $C_1$ to $C_6$ fluoroalkyls, $C_2$ to $C_6$ fluoroalkenyls, $C_7$ to $C_{18}$ fluoroalkylaryls in a more particular embodiment; and hydrogen radical, fluorine radical, chlorine radical, methyl, ethyl, propyl, isopropyl, butyl, isobutyl, tertiary butyl, hexyl, phenyl, 2,6-di-methylpheyl, and 4-tertiarybutylpheyl groups in yet a more particular embodiment; wherein adjacent R groups may form a ring, either saturated, partially saturated, or completely saturated.

The structure of the metallocene catalyst component represented by (XIIIa) may take on many forms such as disclosed in, for example, U.S. Pat. No. 5,026,798, U.S. Pat. No. 5,703,187, and U.S. Pat. No. 5,747,406, including a dimmer or oligomeric structure, such as disclosed in, for example, U.S. Pat. No. 5,026,798 and U.S. Pat. No. 6,069,213.

In a particular embodiment of the metallocene represented in (XIIId), $R^1$ and $R^2$ form a conjugated 6-membered carbon ring system that may or may not be substituted.

Non-limiting examples of metallocene catalyst components consistent with the description herein include:

cyclopentadienylzirconium $X_n$,
indenylzirconium $X_n$,
(1-methylindenyl)zirconium $X_n$,
(2-methylindenyl)zirconium $X_n$,
(1-propylindenyl)zirconium $X_n$,
(2-propylindenyl)zirconium $X_n$,
(1-butylindenyl)zirconium $X_n$,
(2-butylindenyl)zirconium $X_n$,
(methylcyclopentadienyl)zirconium $X_n$,
tetrahydroindenylzirconium $X_n$,
(pentamethylcyclopentadienyl)zirconium $X_n$,
cyclopentadienylzirconium $X_n$,
pentamethylcyclopentadienyltitanium $X_n$,
tetramethylcyclopentyltitanium $X_n$,
1,2,4-trimethylcyclopentadienylzirconium $X_n$,
dimethylsilyl(1,2,3,4-tetramethylcyclopentadienyl)(cyclopentadienyl)zirconium $X_n$,
dimethylsilyl(1,2,3,4-tetramethylcyclopentadienyl)(1,2,3-trimethyl-cyclopentadienyl)zirconium $X_n$,
dimethylsilyl(1,2,3,4-tetramethylcyclopentadienyl)(1,2-dimethyl-cyclopentadienyl)zirconium $X_n$,
dimethylsilyl(1,2,3,4-tetramethyl-cyclopentadienyl)(2-methylcyclopentadienyl)zirconium $X_n$,
dimethylsilyl(cyclopentadienyl)(indenyl)zirconium $X_n$,
dimethylsilyl(2-methylindenyl)(fluorenyl)zirconium $X_n$,
diphenylsilyl(1,2,3,4-tetramethyl-cyclopentadienyl)(3-propylcyclopentadienyl)zirconium $X_n$,
dimethylsilyl(1,2,3,4-tetramethylcyclopentadienyl)(3-t-butylcyclopentadienyl)zirconium $X_n$,
dimethylgermyl(1,2-dimethylcyclopentadienyl)(3-isopropylcyclopentadienyl)zirconium $X_n$,
dimethylsilyl(1,2,3,4-tetramethyl-cyclopentadienyl)(3-methylcyclopentadienyl) zirconium $X_n$,
diphenylmethylidene(cyclopentadienyl)(9-fluorenyl)zirconium $X_n$,
diphenylmethylidene(cyclopentadienyl)(indenyl)zirconium $X_n$,
iso-propylidenebis(cyclopentadienyl)zirconium $X_n$,
iso-propylidene(cyclopentadienyl)(9-fluorenyl)zirconium $X_n$,
iso-propylidene(3-methylcyclopentadienyl)(9-fluorenyl)zirconium $X_n$,
ethylenebis(9-fluorenyl)zirconium $X_n$,
meso-ethylenebis(1-indenyl)zirconium $X_n$,
ethylenebis(1-indenyl)zirconium $X_n$,
ethylenebis(2-methyl-1-indenyl)zirconium $X_n$,
ethylenebis(2-methyl-4,5,6,7-tetrahydro-1-indenyl)zirconium $X_n$,
ethylenebis(2-propyl-4,5,6,7-tetrahydro-1-indenyl)zirconium $X_n$,
ethylenebis(2-isopropyl-4,5,6,7-tetrahydro-1-indenyl)zirconium $X_n$,
ethylenebis(2-butyl-4,5,6,7-tetrahydro-1-indenyl)zirconium $X_n$,
ethylenebis(2-isobutyl-4,5,6,7-tetrahydro-1-indenyl)zirconium $X_n$,
dimethylsilyl(4,5,6,7-tetrahydro-1-indenyl)zirconium $X_n$,
diphenyl(4,5,6,7-tetrahydro-1-indenyl)zirconium $X_n$,
ethylenebis(4,5,6,7-tetrahydro-1-indenyl)zirconium $X_n$,
dimethylsilylbis(cyclopentadienyl)zirconium $X_n$,
dimethylsilylbis(9-fluorenyl)zirconium $X_n$,
dimethylsilylbis(1-indenyl)zirconium $X_n$,
dimethylsilylbis(2-methylindenyl)zirconium $X_n$,
dimethylsilylbis(2-propylindenyl)zirconium $X_n$,
dimethylsilylbis(2-butylindenyl)zirconium $X_n$,
diphenylsilylbis(2-methylindenyl)zirconium $X_n$,
diphenylsilylbis(2-propylindenyl)zirconium $X_n$,
diphenylsilylbis(2-butylindenyl)zirconium $X_n$,
dimethylgermylbis(2-methylindenyl)zirconium X,
dimethylsilylbis(tetrahydroindenyl)zirconium $X_n$,
dimethylsilylbis(tetramethylcyclopentadienyl)zirconium $X_n$,
dimethylsilyl(cyclopentadienyl)(9-fluorenyl)zirconium $X_n$,
diphenylsilyl(cyclopentadienyl)(9-fluorenyl)zirconium $X_n$,
diphenylsilylbis(indenyl)zirconium $X_n$,
cyclotrimethylenesilyl(tetramethylcyclopentadienyl)(cyclopentadienyl)zirconium $X_n$,
cyclotetramethylenesilyl(tetramethylcyclopentadienyl)(cyclopentadienyl) zirconium $X_n$,
cyclotrimethylenesilyl(tetramethylcyclopentadienyl)(2-methylindenyl)zirconium $X_n$,
cyclotrimethylenesilyl(tetramethylcyclopentadienyl)(3-methylcyclopentadienyl)zirconium $X_n$,
cyclotrimethylenesilylbis(2-methylindenyl)zirconium $X_n$,
cyclotrimethylenesilyl(tetramethylcyclopentadienyl)(2,3,5-trimethylcyclopentadienyl)zirconium $X_n$,
cyclotrimethylenesilylbis(tetramethylcyclopentadienyl)zirconium $X_n$,
dimethylsilyl(tetramethylcyclopentadieneyl)(N-tert-butylamido)titanium $X_n$,
bis(cyclopentadienyl)chromium $X_n$,
bis(cyclopentadienyl)zirconium $X_n$,
bis(n-butylcyclopentadienyl)zirconium $X_n$,
bis(n-dodecyclcyclopentadienyl)zirconium $X_n$,
bis(ethylcyclopentadienyl)zirconium $X_n$,
bis(iso-butylcyclopentadienyl)zirconium $X_n$,
bis(iso-propylcyclopentadienyl)zirconium $X_n$,
bis(methylcyclopentadienyl)zirconium $X_n$,
bis(n-oxtylcyclopentadienyl)zirconium $X_n$,
bis(n-pentylcyclopentadienyl)zirconium $X_n$,
bis(n-propylcyclopentadienyl)zirconium $X_n$,
bis(trimethylsilylcyclopentadienyl)zirconium $X_n$,
bis(1,3-bis(trimethylsilyl)cyclopentadienyl)zirconium $X_n$,
bis(1-ethyl-2-methylcyclopentadienyl)zirconium $X_n$,
bis(1-ethyl-3-methylcyclopentadienyl)zirconium $X_n$,
bis(pentamethylcyclopentadienyl)zirconium $X_n$,
bis(pentamethylcyclopentadienyl)zirconium $X_n$,
bis(1-propyl-3-methylcyclopentadienyl)zirconium $X_n$,
bis(1-n-butyl-3-methylcyclopentadienyl)zirconium $X_n$,
bis(1-isobutyl-3-methylcyclopentadienyl)zirconium $X_n$,
bis(1-propyl-3-butylcyclopentadienyl)zirconium $X_n$,
bis(1,3-n-butylcyclopentadienyl)zirconium $X_n$,
bis(4,7-dimethylindenyl)zirconium $X_n$,
bis(indenyl)zirconium $X_n$,
bis(2-methylindenyl)zirconium $X_n$,
cyclopentadienylindenylzirconium $X_n$,
bis(n-propylcyclopentadienyl)hafnium $X_n$,
bis(n-butylcyclopentadienyl)hafnium $X_n$,
bis(n-pentylcyclopentadienyl)hafnium $X_n$,
(n-propyl cyclopentadienyl)(n-butyl cyclopentadienyl)hafnium $X_n$,
bis[(2-trimethylsilylethyl)cyclopentadienyl]hafnium $X_n$,
bis(trimethylsilyl cyclopentadienyl)hafnium $X_n$,
bis(2-n-propylindenyl)hafnium $X_n$,
bis(2-n-butylindenyl)hafnium $X_n$,
dimethylsilylbis(n-propylcyclopentadienyl)hafnium $X_n$,
dimethylsilylbis(n-butylcyclopentadienyl)hafnium $X_n$,
bis(9-n-propylfluorenyl)hafnium $X_n$,
bis(9-n-butylfluorenyl)hafnium $X_n$,
(9-n-propylfluorenyl)(2-n-propylindenyl)hafnium $X_n$,
bis(1-n-propyl-2-methylcyclopentadienyl)hafnium $X_n$,
(n-propylcyclopentadienyl)(1-n-propyl-3-n-butylcyclopentadienyl)hafnium $X_n$, dimethylsilyl(tetramethylcyclopentadienyl)(cyclopropylamido)titanium $X_n$,
dimethylsilyl(tetramethyleyclopentadienyl)(cyclobutylamido)titanium $X_n$,
dimethylsilyl(tetramethyleyclopentadienyl)(cyclopentylamido)titanium $X_n$,
dimethylsilyl(tetramethylcyclopentadienyl)(cyclohexylamido)titanium $X_n$,
dimethylsilyl(tetramethylcyclopentadienyl)(cycloheptylamido)titanium $X_n$,
dimethylsilyl(tetramethylcyclopentadienyl)(cyclooctylamido)titanium $X_n$,
dimethylsilyl(tetramethylcyclopentadienyl)(cyclononylamido)titanium $X_n$,
dimethylsilyl(tetramethylcyclopentadienyl)(cyclodecylamido)titanium $X_n$,
dimethylsilyl(tetramethylcyclopentadienyl)(cycloundecylamido)titanium $X_n$,
dimethylsilyl(tetramethylcyclopentadienyl)(cyclododecylamido)titanium $X_n$,
dimethylsilyl(tetramethylcyclopentadienyl)(sec-butylamido)titanium $X_n$,
dimethylsilyl(tetramethylcyclopentadienyl)(n-octylamido)titanium $X_n$,
dimethylsilyl(tetramethylcyclopentadienyl)(n-decylamido)titanium $X_n$,
dimethylsilyl(tetramethylcyclopentadienyl)(n-octadecylamido)titanium $X_n$,
methylphenylsilyl(tetramethylcyclopentadienyl)(cyclopropylamido)titanium $X_n$,
methylphenylsilyl(tetramethylcyclopentadienyl)(cyclobutylamido)titanium $X_n$,
methylphenylsilyl(tetramethylcyclopentadienyl)(cyclopentylamido)titanium $X_n$,
methylphenylsilyl(tetramethylcyclopentadienyl)(cyclohexylamido)titanium $X_n$,
methylphenylsilyl(tetramethylcyclopentadienyl)(cycloheptylamido)titanium $X_n$,
methylphenylsilyl(tetramethylcyclopentadienyl)(cyclooctylamido)titanium $X_n$,
methylphenylsilyl(tetramethylcyclopentadienyl)(cyclononylamido)titanium $X_n$,
methylphenylsilyl(tetramethylcyclopentadienyl)(cyclodecylamido)titanium, $X_n$,
methylphenylsilyl(tetramethylcyclopentadienyl)(cycloundecylamido)titanium $X_n$,
methylphenylsilyl(tetramethylcyclopentadienyl)(cyclododecylamido)titanium $X_n$,
methylphenylsilyl(tetramethylcyclopentadienyl)(sec-butylamido)titanium $X_n$,
methylphenylsilyl(tetramethylcyclopentadienyl)(n-octylamido)titanium $X_n$,
methylphenylsilyl(tetramethylcyclopentadienyl)(n-decylamido)titanium $X_n$,
methylphenylsilyl(tetramethylcyclopentadienyl)(n-octadecylamido)titanium $X_n$,
diphenylsilyl(tetramethylcyclopentadienyl)(cyclopropylamido)titanium $X_n$,
diphenylsilyl(tetramethylcyclopentadienyl)(cyclobutylamido)titanium $X_n$,
diphenylsilyl(tetramethylcyclopentadienyl)(cyclopentylamido)titanium $X_n$,
diphenylsilyl(tetramethylcyclopentadienyl)(cyclohexylamido)titanium $X_n$,
diphenylsilyl(tetramethylcyclopentadienyl)(cycloheptylamido)titanium $X_n$,
diphenylsilyl(tetramethylcyclopentadienyl)(cyclooctylamido)titanium $X_n$,
diphenylsilyl(tetramethylcyclopentadienyl)(cyclononylamido)titanium $X_n$,
diphenylsilyl(tetramethylcyclopentadienyl)(cyclodecylamido)titanium $X_n$,
diphenylsilyl(tetramethylcyclopentadienyl)(cycloundecylamido)titanium $X_n$,
diphenylsilyl(tetramethylcyclopentadienyl)(cyclododecylamido)titanium $X_n$,
diphenylsilyl(tetramethylcyclopentadienyl)(sec-butylamido)titanium $X_n$,
diphenylsilyl(tetramethyleyclopentadienyl)(n-octylamido)titanium $X_n$,
diphenylsilyl(tetramethyleyclopentadienyl)(n-decylamido)titanium $X_n$,
diphenylsilyl(tetramethylcyclopentadienyl)(n-octadecylamido)titanium $X_n$, and derivatives thereof.

By "derivatives thereof", it is meant any substitution or ring formation as described above; and in particular, replacement of the metal "M" (Cr, Zr, Ti or Hf) with an atom selected from the group consisting of Cr, Zr, Hf and Ti; and replacement of the "X" group with any of $C_1$ to $C_5$ alkyls, $C_6$ aryls, $C_6$ to $C_{10}$ alkylaryls, fluorine or chlorine; n is 1, 2 or 3.

It is contemplated that the metallocene catalysts components described above include their structural or optical or enantiomeric isomers (racemic mixture), and may be a pure enantiomer in one embodiment.

As used herein, a single, bridged, asymmetrically substituted metallocene catalyst component having a racemic and/or meso isomer does not, itself, constitute at least two different bridged, metallocene catalyst components.

As mentioned above, the "metallocene catalyst component" may comprise any combination of any "embodiment" described herein.

Phenoxide Transition Metal Catalyst Compositions

Phenoxide transition metal catalyst compositions are heteroatom substituted phenoxide ligated Group 3 to 10 transition metal or lanthanide metal compounds wherein the metal is bound to the oxygen of the phenoxide group. Phenoxide transition metal catalyst compounds may be represented by Formula XIV or XV:

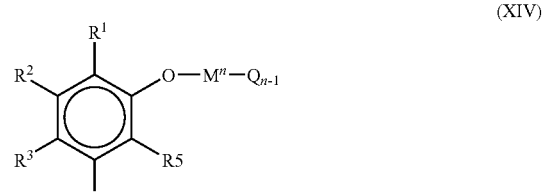

(XIV)

or

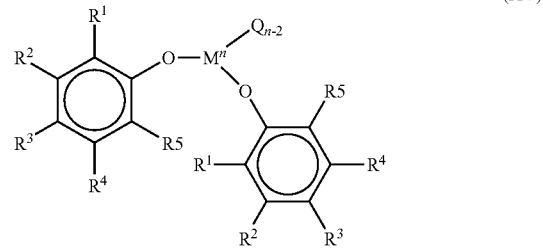

(XV)

wherein $R^1$ is hydrogen or a $C_4$ to $C_{100}$ group, preferably a tertiary alkyl group, preferably a $C_4$ to $C_{20}$ alkyl group, preferably a $C_4$ to $C_{20}$ tertiary alkyl group, preferably a neutral $C_4$ to $C_{100}$ group and may or may not also be bound to M;

at least one of $R^2$ to $R^5$ is a heteroatom containing group, the rest of $R^2$ to $R^5$ are independently hydrogen or a $C_1$ to $C_{100}$ group, preferably a $C_4$ to $C_{20}$ alkyl group, preferred examples of which include butyl, isobutyl, t-butyl, pentyl, hexyl, heptyl, isohexyl, octyl, isooctyl, decyl, nonyl, dodecyl, and any of $R^2$ to $R^5$ also may or may not be bound to M;

Each $R^1$ to $R^5$ group may be independently substituted or unsubstituted with other atoms, including heteroatoms or heteroatom containing group(s);

O is oxygen;

M is a Group 3 to Group 10 transition metal or lanthanide metal, preferably a Group 4 metal, preferably M is Ti, Zr or Hf;

n is the valence state of the metal M, preferably 2, 3, 4, or 5; and

Q is, and each Q may be independently be, an alkyl, halogen, benzyl, amide, carboxylate, carbamate, thiolate, hydride or alkoxide group, or a bond to an R group containing a heteroatom which may be any of $R^1$ to $R^5$.

A heteroatom containing group may be any heteroatom or a heteroatom bound to carbon, silicon or another heteroatom. Preferred heteroatoms include boron, aluminum, silicon, nitrogen, phosphorus, arsenic, tin, lead, antimony, oxygen, selenium, and tellurium. Particularly preferred heteroatoms include nitrogen, oxygen, phosphorus, and sulfur. Even more particularly preferred heteroatoms include nitrogen and oxygen. The heteroatom itself may be directly bound to the phenoxide ring or it may be bound to another atom or atoms that are bound to the phenoxide ring. The heteroatom containing group may contain one or more of the same or different heteroatoms. Preferred heteroatom containing groups include imines, amines, oxides, phosphines, ethers, ketones, oxoazolines heterocyclics, oxazolines, thioethers, and the like. Particularly preferred heteroatom containing groups include imines. Any two adjacent R groups may form a ring structure, preferably a 5 or 6 membered ring. Likewise the R groups may form multi-ring structures. In one embodiment any two or more R groups do not form a 5 membered ring.

In a preferred embodiment the heteroatom substituted phenoxide transition metal compound is an iminophenoxide Group 4 transition metal compound, and more preferably an iminophenoxidezirconium compound.

Supported Catalyst Systems

The mixed catalyst system may further include a support or carrier. Each component of the mixed catalyst system may be supported on a support or carrier or each catalyst component may be unsupported. In other words, any one, none, or all of the catalyst components may be supported or unsupported. Further, one of the catalyst components (e.g., the non-metallocene) may reside on one collection of support particles, and another catalyst component (e.g., the metallocene) may reside on another collection of support particles. The support for each of the individual components may be the same or different.

The term "supported" as used herein refers to one or more compounds that are deposited on, contacted with, vaporized with, bonded to, or incorporated within, adsorbed or absorbed in, or on, a support or carrier. The terms "support" or "carrier" for purposes of this specification are used interchangeably and are any support material, preferably a porous support material, including inorganic or organic support materials.

Non-limiting examples of inorganic support materials include inorganic oxides and inorganic chlorides. Other carriers include resinous support materials such as polystyrene, functionalized or crosslinked organic supports, such as polystyrene, divinyl benzene, polyolefins, or polymeric compounds, zeolites, talc, clays, or any other organic or inorganic support material and the like, or mixtures thereof.

The support materials utilized may be any of the conventional support materials. Preferably the supported material is a porous support material, for example, talc, inorganic oxides and inorganic chlorides. Other support materials include resinous support materials such as polystyrene, functionalized or crosslinked organic supports, such as polystyrene divinyl benzene polyolefins or polymeric compounds, zeolites, clays, or any other organic or inorganic support material and the like, or mixtures thereof.

The preferred support materials are inorganic oxides that include those Group 2, 3, 4, 5, 13 or 14 metal oxides. The preferred supports include silica, fumed silica, alumina, silica-alumina and mixtures thereof. Other useful supports include magnesia, titania, zirconia, magnesium chloride, montmorillonite, phyllosilicate, zeolites, talc, clays and the like. Also, combinations of these support materials may be used, for example, silica-chromium, silica-alumina, silica-titania and the like. Additional support materials may include those porous acrylic polymers. Other support materials include nanocomposites, aerogels, spherulites, and polymeric beads. Another support is fumed silica available under the trade name Cabosil™ TS-610, available from Cabot Corporation. Fumed silica is typically a silica with particles 7 to 30 nanometers in size that has been treated with dimethylsilyldichloride such that a majority of the surface hydroxyl groups are capped.

In another embodiment, any of the conventionally known inorganic oxides, such as silica, support materials that retain hydroxyl groups after dehydration treatment methods will be suitable in accordance with the invention. Because of availability, both of silica and silica containing metal oxide based supports, for example, silica-alumina, are preferred. Silica particles, gels and glass beads are most typical.

These metal oxide compositions may additionally contain oxides of other metals, such as those of Al, K, Mg, Na, Si, Ti and Zr and should preferably be treated by thermal and/or chemical means to remove water and free oxygen. Typically such treatment is in a vacuum in a heated oven, in a heated fluidized bed or with dehydrating agents such as organo silanes, siloxanes, alkyl aluminum compounds, etc. The level of treatment should be such that as much retained moisture and oxygen as is possible is removed, but that a chemically significant amount of hydroxyl functionality is retained. Thus calcining at up to 800° C. or more up to a point prior to decomposition of the support material, for several hours is permissible, and if higher loading of supported anionic activator is desired, lower calcining temperatures for lesser times will be suitable. Where the metal oxide is silica, loadings to achieve from less than 0.1 mmol to 3.0 mmol activator/g $SiO_2$ are typically suitable and can be achieved, for example, by varying the temperature of calcining from 200° C. to 1,000° C., such as from 300° C. to 900° C., 400° C. to 875° C., 500° C. to 850° C., 600° C. to 825° C., 700° C. to 800° C., and any combination of any limit with any lower limit.

The tailoring of hydroxyl groups available as attachment sites in this invention can also be accomplished by the pre-treatment with a less than stoichiometric amount of a chemical dehydrating agent. If calcining temperatures below 400° C. are employed, difunctional coupling agents (e.g., $(CH_3)_3SiCl_2$) may be employed to cap hydrogen bonded pairs of silanol groups which are present under the less severe calcining conditions. Similarly, use of the Lewis acid in excess of the stoichiometric amount needed for reaction with the transition metal compounds will serve to neutralize excess silanol groups without significant detrimental effect for catalyst preparation or subsequent polymerization.

In another embodiment, the support is a polymeric support, including hydroxyl-functional-group-containing polymeric substrates, but functional groups may be any of the primary alkyl amines, secondary alkyl amines, and others, where the groups are structurally incorporated in a polymeric chain and capable of a acid-base reaction with the Lewis acid such that a ligand filling one coordination site of the aluminum is protonated and replaced by the polymer incorporated functionality. See, for example, the functional group containing polymers of U.S. Pat. No. 5,288,677.

It is preferred that the support material, most preferably an inorganic oxide, has a surface area in the range of from about 10 to about 700 m$^2$/g, pore volume in the range of from about 0.1 to about 4.0 cc/g and average particle size in the range of from about 5 to about 500 μm. More preferably, the surface area of the support material is in the range of from about 50 to about 500 m$^2$/g, pore volume of from about 0.5 to about 3.5 cc/g and average particle size of from about 10 to about 200l m. The average pore size of the carrier is typically in the range of from 10 to 1000 Å, preferably 50 to about 500 Å, and most preferably 75 to about 350 Å.

The support materials may be treated chemically, for example with a fluoride compound as described in WO 00/12565. Other supported activators are described in for example WO 00/13792 that refers to supported boron containing solid acid complex.

In another embodiment, an antistatic agent or surface modifier that is used in the preparation of the supported catalyst system as described in PCT publication WO 96/11960 may be used with catalyst systems including the activator compounds described herein. The catalyst systems may also be prepared in the presence of an olefin, for example 1-hexene.

In another embodiment, the activator and/or catalyst system may be combined with a carboxylic acid salt of a metal ester, for example aluminum carboxylates such as aluminum mono, di- and tri-stearates, aluminum octoates, oleates and cyclohexylbutyrates, as described in U.S. Pat. Nos. 6,300,436 and 6,306,984.

Method For Supporting

Various methods can be used to affix two catalyst components to a support to form the mixed catalyst system. For example, one procedure includes forming a mixture (solution or slurry) of the first catalyst component and a non-polar hydrocarbon, and contacting this mixture with a mixture (solution or slurry) that includes the second catalyst component.

In one aspect, the support is prepared by heating support particles at a dehydration temperature of up to 600° C., or to 800° C. or more when preparing an "enhanced support," resulting in a support having a modified chemical structure, e.g., a reduced number of hydroxyl groups. The higher dehydration temperatures are preferred.

The support is preferably an inorganic material such as silicon oxide (silica) or aluminum oxide. The support material can be a dry powder, and in certain embodiments has an average particle size of from 1-500 microns, or more narrowly from 10-250 microns. The surface area of the support may range from 3 m 2/g to 600 m$^2$/g or more.

A preferred support is an amorphous high surface area silica, such as Davison 952 or Sylopol® 955, sold by Davison Chemical Division of W.R. Grace and Company. Those silicas are in spherical form, prepared by a spray drying process, with a surface area of about 300 m$^2$/g and a pore volume of about 1.65 cm$^3$/g. A procedure for dehydrating the silica at 600° C. or more is set forth in U.S. Pat. No. 5,525,678.

A variety of non-polar hydrocarbons can be used to form the support slurry, but any non-polar hydrocarbon selected should remain in liquid form at all relevant reaction temperatures, and the ingredients used to form the first catalyst component should be at least partially soluble in the non-polar hydrocarbon. Accordingly, the non-polar hydrocarbon is considered to be a "solvent" herein, even though in certain embodiments the ingredients are only partially soluble in the hydrocarbon. For example, the organomagnesium compound, alcohol and transition metal compound of the first catalyst compound, described above, should be at least partially soluble, and preferably completely soluble, in that hydrocarbon solvent at the mixing temperatures described above.

Examples of suitable non-polar hydrocarbons include $C_4$-$C_{10}$ linear or branched alkanes, cycloalkanes and aromatics. More specifically, a non-polar alkane can be isopentane, hexane, isohexane, n-heptane, octane, nonane, or decane; a non-polar cycloalkane such as cyclohexane; or an aromatic such as benzene, toluene, or ethylbenzene. Mixtures of different non-polar hydrocarbons can also be used.

The support slurry can be heated both during and after mixing of the support particles with the non-polar hydrocarbon solvent, but at the point when either or both of the catalysts are combined with the support slurry, the temperature of the slurry should be sufficiently low so that neither of the catalysts are inadvertently activated. Thus, the temperature of the support slurry (e.g., silica slurry) is preferably maintained at a temperature below 90° C., e.g., from 25 to 70° C., or even more narrowly from 40 to 60° C.

Activator

The term "activator" as used herein refers to any compound or component, or combination of compounds or components, capable of enhancing the ability of a catalyst to polymerize olefin monomers to form polyolefins. In certain embodiments, either or both of the catalyst components may be contacted with a catalyst activator, herein simply referred to as an "activator."

The activator may be any one or a combination of compounds commonly employed to activate Group 15-containing catalysts. These include metal alkyls, hydrides, alkylhydrides, alkylhalides (such as alkyllithium compounds), dialkylzinc compounds, trialkylboron compounds, trialkylaluminum compounds, alkylaluminum halides, alkylaluminum and hydrides, and tetraalkylgermanium compounds. Preferably, this activator is trimethyl aluminum (TMA). The amount of activator is preferably sufficient to give a molar ratio of activator to metal in the catalyst component of about 3:1 to about 1000:1, preferably about 15:1 to about 300:1, and most preferably about 20:1 to about 100:1.

The activator may also be any one or a combination of compounds suitable for activating the metal sites of the metallocene type catalyst which may be different from the activator described above. This second activator is preferably a linear and/or cyclic aluminoxane species prepared from the interaction of $R_3Al$ and water, where R is a $C_1$-$C_{12}$ linear, branched or cyclic alkyl, with the amount of water controlling the average molecular weight of the aluminoxane molecule. Preferably, methylaluminoxane (MAO) is used.

Polymerization Process

The activators and the polymerization catalysts described above, whether supported or not, are suitable for use in any prepolymerization and/or polymerization process over a wide range of temperatures and pressures. The temperatures may be in the range of from −60° C. to about 280° C., preferably from 50° C. to about 200° C. In one embodiment, the polymerization temperature is above 0° C., above 50° C., above 80° C., above 100° C., above 150° C., or above 200° C. In one embodiment, the pressures employed may be in the range from 1 atmosphere to about 500 atmospheres or higher.

Polymerization processes include solution, gas phase, slurry phase, and a high pressure process, or a combination thereof. Particularly preferred is a gas phase or slurry phase polymerization of one or more olefin(s) at least one of which is ethylene or propylene.

In one embodiment, the process is a solution, high pressure, slurry or gas phase polymerization process of one or more olefin monomers having from 2 to 30 carbon atoms, preferably 2 to 12 carbon atoms, and more preferably 2 to 8 carbon atoms. The invention is particularly well suited to the polymerization of two or more olefin monomers of ethylene, propylene, 1-butene, 1-pentene, 4-methyl-1-pentene, 1-hexene, 1-octene and 1-decene.

Other monomers useful include ethylenically unsaturated monomers, diolefins having 4 to 18 carbon atoms, conjugated or nonconjugated dienes, polyenes, vinyl monomers and cyclic olefins. Non-limiting monomers useful in the invention may include norbornene, norbornadiene, isobutylene, isoprene, vinylbenzocyclobutane, styrenes, alkyl substituted styrene, ethylidene norbornene, dicyclopentadiene and cyclopentene.

In another embodiment, a copolymer of ethylene is produced, where with ethylene, a comonomer having at least one alpha-olefin having from 4 to 15 carbon atoms, preferably from 4 to 12 carbon atoms, and most preferably from 4 to 8 carbon atoms, is polymerized in a gas phase process.

In another embodiment, ethylene or propylene is polymerized with at least two different comonomers, optionally one of which may be a diene, to form a terpolymer.

In one embodiment, the invention is directed to a polymerization process, particularly a gas phase or slurry phase process, for polymerizing propylene alone or with one or more other monomers including ethylene, and/or other olefins having from 4 to 12 carbon atoms.

Typically in a gas phase polymerization process, a continuous cycle is employed where in one part of the cycle of a reactor system, a cycling gas stream, otherwise known as a recycle stream or fluidizing medium, is heated in the reactor by the heat of polymerization. This heat is removed from the recycle composition in another part of the cycle by a cooling system external to the reactor. Generally, in a gas fluidized bed process for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer.

The reactor pressure in a gas phase process may vary from about 100 psig (690 kPa) to about 500 psig (3448 kPa), preferably in the range of from about 200 psig (1379 kPa) to about 400 psig (2759 kPa), more preferably in the range of from about 250 psig (1724 kPa) to about 350 psig (2414 kPa).

The reactor temperature in a gas phase process may vary from about 30° C. to about 120° C., preferably from about 60° C. to about 115° C., more preferably in the range of from about 70° C. to 110° C., and most preferably in the range of from about 70° C. to about 95° C. In another embodiment, the reactor temperature in a gas phase process is above 60° C.

Other gas phase processes include series or multistage polymerization processes. Gas phase processes may also include those described in U.S. Pat. Nos. 5,627,242, 5,665,818 and 5,677,375, and European publications EP-A-0 794 200 EP-B1-0 649 992, EP-A-0 802 202 and EP-B-634 421.

In another embodiment, the process may produce greater than 500 lbs of polymer per hour (227 Kg/hr) to about 200,000 lbs/hr (90,900 Kg/hr) or higher of polymer, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and most preferably greater than 65,000 lbs/hr (29,000 Kg/hr) to greater than 100,000 lbs/hr (45,500 Kg/hr).

A slurry polymerization process generally uses pressures in the range of from about 1 to about 50 atmospheres and even greater and temperatures in the range of 0° C. to about 120° C. In another embodiment, the slurry process temperature is above 100° C. In a slurry polymerization, a suspension of solid, particulate polymer is formed in a liquid polymerization diluent medium to which ethylene and comonomers and often hydrogen along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process must be operated above the reaction diluent critical temperature and pressure. Preferably, a hexane or an isobutane medium is employed.

In another embodiment, the polymerization technique is referred to as a particle form polymerization, or a slurry process where the temperature is kept below the temperature at which the polymer goes into solution. Such technique is well known in the art, and described in for instance U.S. Pat. No. 3,248,179. Other slurry processes include those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484.

In another embodiment, this process may produce greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor may produce greater than 15,000 lbs of polymer per hour (6804 Kg/hr), preferably greater than 25,000 lbs/hr (11,340 Kg/hr) to about 100,000 lbs/hr (45,500 Kg/hr).

Examples of solution processes are described in U.S. Pat. Nos. 4,271,060, 5,001,205, 5,236,998 and 5,589,555 and PCT WO 99/32525.

In one embodiment, the slurry or gas phase process is operated in the presence of the catalyst system described herein and in the absence of or essentially free of any scavengers, such as triethylaluminum, trimethylaluminum, tri-isobutylaluminum and tri-n-hexylaluminum and diethyl aluminum chloride, dibutyl zinc and the like. This process is described in PCT publication WO 96/08520 and U.S. Pat. Nos. 5,712,352 and 5,763,543.

In another embodiment, the method provides for injecting the catalyst system described herein into a reactor, particularly a gas phase reactor. In one embodiment the catalyst system is used in the unsupported form, preferably in a liquid form such as described in U.S. Pat. Nos. 5,317,036 and 5,693,727 and European publication EP-A-0 593 083. The polymerization catalyst in liquid form can be fed with an activator, and/or a support, and/or a supported activator together or separately to a reactor. The injection methods described in PCT publication WO 97/46599 may be utilized.

Where an unsupported catalyst system is used the mole ratio of the metal of the activator component to the metal of the catalyst compound is in the range of between 0.3:1 to 10,000:1, preferably 100:1 to 5000:1, and most preferably 500:1 to 2000:1.

Polymer Products

The polymers produced can be used in a wide variety of products and end-use applications. The polymers produced include polyethylene homopolymers and polyethylene copolymers, including linear low density polyethylene, elastomers, plastomers, high density polyethylenes, medium density polyethylenes, low density polyethylenes, as well as polypropylene homopolymers and polypropylene co polymers.

The polymers, typically ethylene based polymers, have a density in the range of from 0.86 g/cc to 0.97 g/cc, preferably in the range of from 0.88 g/cc to 0.965 g/cc, more preferably in the range of from 0.900 g/cc to 0.96 g/cc, even more preferably in the range of from 0.905 g/cc to 0.95 g/cc, yet even more preferably in the range from 0.910 g/cc to 0.940 g/cc, and most preferably greater than 0.915 g/cc, preferably greater than 0.920 g/cc, and most preferably greater than 0.925 g/cc. Density is measured in accordance with ASTM-D-1238.

The polymers produced typically have a molecular weight distribution, a weight average molecular weight to number average molecular weight ($M_w/M_n$) of greater than 1.5 to about 15, particularly greater than 2 to about 10, more preferably greater than about 2.2 to less than about 8, and most preferably from 2.5 to 8. The polymers may have a narrow molecular weight distribution and a broad composition distribution or vice-versa, and may be those polymers described in U.S. Pat. No. 5,798,427.

Also, the polymers typically have a narrow composition distribution as measured by Composition Distribution Breadth Index (CDBI). Further details of determining the CDBI of a copolymer are known to those skilled in the art. See, for example, PCT Patent Application WO 93/03093, published Feb. 18, 1993. The polymers in one embodiment have CDBI's generally in the range of greater than 50% to 100%, preferably 99%, preferably in the range of 55% to 85%, and more preferably 60% to 80%, even more preferably greater than 60%, still even more preferably greater than 65%. In another embodiment, polymers produced using a catalyst system described herein have a CDBI less than 50%, more preferably less than 40%, and most preferably less than 30%.

The polymers in one embodiment have a melt index (MI) or ($I_2$) as measured by ASTM-D-1238-E (190/2.16) in the range from no measurable flow to 1000 dg/min, more preferably from about 0.01 dg/min to about 100 dg/min, even more preferably from about 0.1 dg/min to about 50 dg/min, and most preferably from about 0.1 dg/min to about 10 dg/min.

In one embodiment, the polymers have a melt index ratio ($I_{21}/I_2$) ($I_{21}$ is measured by ASTM-D-1238-F) (190/21.6) of from 10 to less than 25, more preferably from about 15 to less than 25. The polymers, in a preferred embodiment, have a melt index ratio ($I_{21}/I_2$) of from greater than 25, more preferably greater than 30, even more preferably greater that 40, still even more preferably greater than 50 and most preferably greater than 65. For example, the melt index ratio ($I_{21}/I_2$) may be of from 5 to 300, 10 to 200, 20 to 180, 30 to 160, 40 to 120, 50 to 100, 60 to 90, and a combination of any upper limit with any lower limit.

Bimodal Polymer Product

The polymers produced by the processes described herein, utilizing the mixed catalysts described herein, are preferably bimodal. The term "bimodal," when used to describe a polymer or polymer composition, e.g., polyolefins such as polypropylene or polyethylene, or other homopolymers, copolymers or terpolymers, means "bimodal molecular weight distribution," which term is understood as having the broadest definition persons in the pertinent art have given that term as reflected in printed publications and issued patents. For example, a single composition that includes polyolefins with at least one identifiable high molecular weight distribution and polyolefins with at least one identifiable low molecular weight distribution is considered to be a "bimodal" polyolefin, as that term is used herein. Preferably, other than having different molecular weights, the high molecular weight polyolefin and the low molecular weight polyolefin are essentially the same type of polymer, e.g., polypropylene or polyethylene.

The bimodal polymer products prepared using the mixed catalysts described herein can be used in a wide variety of products and end-use applications. The polymers produced by the process of the invention include linear low density polyethylene, elastomers, plastomers, high density polyethylenes, low density polyethylenes, medium density polyethylenes, polypropylene and polypropylene copolymers.

The bimodal polymers that can be made using the described processes can have a variety of compositions, characteristics and properties. At least one of the advantages of the catalysts is that the process utilized can be tailored to form a polymer composition with a desired set of properties. For example, it is contemplated that the polymers having the same properties as the bimodal polymer compositions in U.S. Pat. No. 5,525,678 can be formed. Also, the bimetallic catalysts described herein can be used in polymerization processes to form polymers having the same properties as the polymers in the following patents, 6,420,580; 6,388,115; 6,380,328; 6,359,072; 6,346,586; 6,340,730; 6,339,134; 6,300,436; 6,274,684; 6,271,323; 6,248,845; 6,245,868; 6,245,705; 6,242,545; 6,211,105; 6,207,606; 6,180,735; and 6,147,173.

The bimodal polymers, typically ethylene based polymers, should have a density in the range of from 0.86 g/cc to 0.97 g/cc, preferably in the range of from 0.88 g/cc to 0.965 g/cc, more preferably in the range of from 0.900 g/cc to 0.96 g/cc, even more preferably in the range of from 0.905 g/cc to 0.955 g/cc, yet even more preferably in the range from 0.910 g/cc to 0.955 g/cc, and most preferably greater than 0.915 g/cc, preferably greater than 0.920 g/cc, and most preferably greater than 0.925 g/cc.

The bimodal polymers can have a molecular weight distribution, a weight average molecular weight to number average molecular weight ($M_w/M_n$) of greater than 5 to about 80, particularly greater than 10 to about 60, more preferably greater than about 15 to less than about 55, and most preferably from 20 to 50.

The bimodal polymers made by the described processes can in certain embodiments have a melt index (MI) or ($I_2$) as measured by ASTM-D-1238-E in the range from 0.01 dg/min to 1000 dg/min, more preferably from about 0.01 dg/min to about 100 dg/min, even more preferably from about 0.02 dg/min to about 50 dg/min, and most preferably from about 0.03 dg/min to about 0.1 dg/min.

The bimodal polymers made by the described processes can in certain embodiments have a melt index ratio ($I_{21}/I_2$) ($I_{21}$ is measured by ASTM-D-1238-F) of from 40 to less than 500, more preferably from about 60 to less than 200.

Expressed differently, bimodal polymers made by the described processes can in certain embodiments have a melt index ratio ($I_{21}/I_2$) ($I_{21}$ is measured by ASTM-D-1238-F) of from preferably greater than 40, more preferably greater than 50, even more preferably greater that 60, still even more preferably greater than 65 and most preferably greater than 70. In one or more other embodiments, the polymer of the invention may have a narrow molecular weight distribution and a broad composition distribution or vice-versa, and may be those polymers described in U.S. Pat. No. 5,798,427.

In certain embodiments, propylene based polymers can be produced using the processes described herein. These polymers include atactic polypropylene, isotactic polypropylene, hemi-isotactic and syndiotactic polypropylene. Other propylene polymers include propylene block or impact copolymers. Propylene polymers of these types are well known in the art see for example U.S. Pat. Nos. 4,794,096, 3,248,455, 4,376,851, 5,036,034 and 5,459,117.

The polymers of the invention may be blended and/or coextruded with any other polymer. Non-limiting examples of other polymers include linear low density polyethylenes produced via conventional Ziegler-Natta and/or bulky ligand metallocene-type catalysis, elastomers, plastomers, high pressure low density polyethylene, high density polyethylenes, polypropylenes and the like.

Polymers produced by the process of the invention and blends thereof are useful in such forming operations as film, sheet, pipe and fiber extrusion and co-extrusion as well as blow molding, injection molding and rotary molding. Films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications. Fibers include melt spinning, solution spinning and melt blown fiber operations for use in woven or non-woven form to make filters, diaper fabrics, medical garments, geotextiles, etc. Extruded articles include medical tubing, wire and cable coatings, geomembranes, and pond liners. Molded articles include single and multi-layered constructions in the form of bottles, tanks, large hollow articles, rigid food containers and toys, etc.

EXAMPLES

In order to provide a better understanding of the foregoing discussion, the following non-limiting examples are offered. Although the examples may be directed to specific embodiments of the present invention, they are not to be viewed as limiting the invention in any specific respect. All parts, proportions, and percentages are by weight unless otherwise indicated. All examples were carried out in dry, oxygen-free environments and solvents. All molecular weights are weight average molecular weight unless otherwise noted. Molecular weights (weight average molecular weight ($M_w$) and number average molecular weight ($M_n$) and ($M_z$) were measured by Gel Permeation Chromatography (GPC).

General Procedure for Synthesis

The catalyst synthesis and preparation is described below. All manipulations, unless otherwise noted, were performed in a nitrogen-filled glove box or using standard Schlenk techniques, unless stated otherwise. The reagents, particularly toluene and hexane were passed through individual sets of one gallon cylinders containing 13X molecular sieves and de-oxo catalyst before use. Deuterated benzene and toluene were dried over NaK alloy. Deuterated benzene, toluene, and tetrahydrofuran were degassed by the freeze-pump-thaw method. (The deuterated tetrahydrofuran was dried over sodium.) MOS (silica-supported MAO, 4.5 mmol Al/g) was obtained from Exxon. Kaydol mineral oil was purged with nitrogen while heated to 200° C. All other reagents were used as received from Aldrich.

In situ reagents were identified by comparison of starting reagents in comparable deuterated solvents. Quantitative internal standards for $^1$H NMR spectra were referenced to protio impurities in the deuterio solvents. $^{19}$F NMR spectra were referenced to −76.55 ppm $CF_3COOH$ external standard solution. $^1$H NMR spectra were obtained from a QE-300 ($^1$H, 300 MHz) at room temperature.

1. Synthesis of "HN3"
$\{(HN(CH_2CH_2NHMesityl)_2)\}$

In dry box, a one liter Schlenk flask equipped with a stirbar was charged with, in the following order, 200 mL of toluene, diethyltriamine (12.31 mL, 114 mmol) bromomesitylene (34.8 mL, 227 mmol), Pd(II) dba (0.523 g, 0.571 mmol), rac-BINAP (1.064 g, 1.7 mmol), Na t-butoxide (32.8 g, 340 mmol), and 200 mL toluene (400 mL toluene total). On a Schlenk line with an argon atmosphere, the dark red heterogeneous solution was equipped with a reflux condenser and heated at 102° C. in an oil bath. After 19 hours, the reaction was removed from the oil bath and allowed to cool to room temperature. The wine colored heterogeneous solution was then transferred to a 2 liter separatory funnel and dissolved in 750 mL ether. The ether solution was washed with water (2×250 mL) and brine (2×250 mL) and then dried over magnesium sulfate. Solvent was removed in vacuo on rotovap. The yellow/amber oil was then placed on Schlenk line and left under vacuum overnight. When the flask was returned to normal atmosphere pressure, the oil turned to clumps. $^1$H NMR confirmed the isolation of the desired product as yellow/amber solids (38.2 g, 98.7% yield). $^1$H NMR ($C_6D_6$): δ 0.73 (br s, 1H), 2.21 (s, 3H), 2.27 (s, 6H), 2.50 (t, 2H), 2.85 (t, 3H), 3.37 (br s, 1H), 6.83 (br s, 2H).

2. Synthesis of HN5
"$\{(HN(CH_2CH_2NHC_6(CH_3)_5)_2)\}$"

In dry box, a one liter Schlenk flask equipped with a stirbar was charged with, in the following order, 200 mL of toluene, Pd(II) dba (0.507 g, 0.553 mmol), rac-BINAP (1.05 g, 1.69 mmol), diethyltriamine (11.36 mL, 110 mmol) bromopentamethylbenzene, (50 g, 220 mmol), Na t-butoxide (31.73 g, 330 mmol), and 200 mL toluene (400 mL toluene total). On a Schlenk line with an argon atmosphere, the dark red heterogeneous solution was equipped with a reflux condenser and heated at 100° C. in an oil bath. After 19 hours, the reaction was removed from the oil bath and allowed to cool to room temperature. The wine colored heterogeneous solution was then transferred to a 2 liter separatory funnel and dissolved in 750 mL ether. The ether solution was washed with water (2×250 mL) and brine (2×250 mL) and then dried over magnesium sulfate. Solvent was removed in vacuo on rotovap. The yellow/amber oil was then placed on Schlenk line and left under vacuum overnight. When the flask was returned to normal atmosphere pressure, the oil turned to clumps. $^1$H NMR confirmed the isolation of the desired product as yellow solids (35.3 g, 86%). $^1$H-NMR (C$_6$D$_6$): δ 0.88 (br s, 1H), 2.14 (s, 3H), 2.150 (s, 6H), 2.32 (s, 6H), 2.62 (t, 2H), 2.87 (t, 2H), 3.47 (br s, 1H).

3. Synthesis of HN3Zr(NMe$_2$)$_2$

To a 50 mL flask, 7 mL of hexane was added to 1.267 g (3.737 mmol) of (1) HN3 and allowed to stir for ten minutes. Tetrakis(dimethylamino)zirconium (1.00 g, 3.737 mmol) was added to the slurry and left to stir for two hours. Volatiles were removed by vacuum from the heterogeneous amber slurry resulting in the isolation of 1.81 g (94%) of a tan precipitate. $^1$H NMR (C$_6$D$_6$): δ 1.80 (m, 1H), 2.21 (s, 6H), 2.28 (s, 6H), 2.45 (s, 6H), 2.47 (s, 6H), 2.59 (m, 4H), 3.00 (m, 2H), 3.05 (s, 6H), 3.35 (s, 2H), 6.95 (br s, 4H).

4. Synthesis of C$_6$F$_5$OSi(CH$_3$)$_3$ n-Butyllithium (9.75 mL, 22.39 mmol, 2.5 M in hexane) was added dropwise, at 0° C., to a 200 mL hexane solution of C$_6$F$_5$OH (4.08 g, 22.17 mmol). After the addition of n-butyllithium was complete, the reaction mixture was allowed to warm to room temperature. Chlorotrimethylsilane (2.65 g, 24.39 mmol) was added to the reaction at −40° C. After slowly warming to room temperature, the reaction was refluxed for 19 hours. Isolation of the crude product was achieved by ether extraction. The organic was washed with ammonium chloride, water, brine, and dried over sodium sulfate. Solvent was removed in vacuo to yield 4.0 g of crude product. The resulting liquid was purified by vacuum distillation to give 3.4 g (60%) of a colorless liquid. $^1$H NMR(C6D6): δ 0.081 (br. s).

5. Synthesis of HN5Zr(NMe$_2$)$_2$ 100 mL of hexane was added to 3.00 g (11.21 mmol) of (2) HN5 and allowed to stir for ten minutes. Tetrakis(dimethylamino)zirconium (4.43 g, 11.21 mmol) was added to the slurry and left to stir for 19 hours. The heterogeneous solution was concentrated to half volume. The resulting tan precipitate was isolated by filtration and the remaining volatiles were removed by vacuum. Total yield of desired product was 5.14 g (80%). $^1$H NMR (C$_6$D$_6$): δ 1.85 (br m, 1H), 2.14 (s, 6H), 2.20 (s, 6H), 2.22 (s, 6H), 2.24 (s, 6H), 2.50 (s, 6H), 2.53 (s, 6H), 2.68 (m, 4H), 3.04 (m, 2H), 3.12 (s, 6H), 3.37 (m, 2H).

Example 1

HN3Zr(OC$_6$F$_5$)$_2$ 9 mL of a 0.05 M stock solution of (3) HN3Zr(NMe$_2$)$_2$ was added to 0.346 g (1.35 mmol) of (4) C$_6$F$_5$OSi(CH$_3$)$_3$ and allowed to stir at room temperature for three days. Volatiles were removed in vacuo from the homogeneous light amber solution leaving a tan sticky paste in the reaction flask. Triturations with hexane resulted in 0.559 g of a crude white solid. When these solids were dissolved in C$_6$D$_6$ for $^1$H NMR analysis, 0.032 g precipitated out of solution and 23.9 mg (9% yield) of the desired product was isolated. The kinetic parameters are listed in Table 5 below. $^1$H NMR (C$_6$D$_6$): δ 2.04 (s, 6H), 2.19 (s, 6H), 2.63 (s, 6H), 2.60 (br m, 4H), 2.82 (m, 2H), 3.33 (m, 2H), 6.70 (s, 2H), 6.73 (s, 2H).

Examples 2 and 3

HN5Zr(NMe$_2$)(OC$_6$F$_5$) and HN5Zr(OC$_6$F$_5$)$_2$ 0.600 g (1.047 mmol) of (5) HN5Zr(NMe$_2$)$_2$ was slowly added to a flask charged with 2.3 g (8.97 mmol) of (4) C$_6$F$_5$OSi(CH$_3$)$_3$ and the amber yellow heterogeneous solution (solution was initially heterogeneous light yellow) was allowed to stir for 2 hours. An equivalent volume of hexane was added to the reaction flask and the hexane insoluble solids were isolated as a tan powder (0.132 g) which, by $^1$H NMR (C$_6$D$_6$) analysis, was the mono substituted product. After 26 days, crystals were observed in the hexane wash and isolated (0.212 g, 29% yield) by decanting away the liquid and drying by vacuum.

A proton NMR study revealed that the crystal contained the following molecules:

[(C$_6$Me$_5$)NCH$_2$CH$_2$NHCH$_2$CH$_2$N(C$_6$Me$_5$)]Zr(OC$_6$F$_5$)$_2$ and [(C$_6$Me$_5$)NCH$_2$CH$_2$NHCH$_2$CH$_2$N(C$_6$Me$_5$)]Zr(OC$_6$F$_5$)$_2$(NMe$_2$H)

$^1$H NMR (C$_6$D$_6$): δ 2.05 (s, 6H), 2.16 (s, 6H), 2.17 (s, 6H), 2.32 (s, 6H), 2.49 (s, 6H), 2.62 (m, 5H), 2.94 (s, 6H), 2.98 (m, 2H), 3.33 (m, 2H).

$^1$H NMR (C$_6$D$_6$): δ 1.97 (s, 6H), 2.02 (s, 6H), 2.12 (s, 6H), 2.19 (s, 6H), 2.42 (s, 6H), 2.72 (br m, 5H), 2.92 (br m, 2H), 3.40 (br m, 2H).

A crystallography of the crystals was also performed. A colorless crystal of dimensions 0.32×0.38×0.45 mm was covered in the perfluoropolyether PFO-XR75 (Lancaster) and sealed under nitrogen in a glass capillary. The crystal was optically aligned on the four-circle of a Siemens P4 diffractometer equipped with a graphite monochromatic crystal, a MoKα radiation source (λ=0.71073 Å), and a SMART CCD detector held at 5.054 cm from the crystal. The sample was cooled to −50° C. with a nitrogen stream produced by a LT-2 low temperature system. Four sets of 20 frames each were collected using the ω scan method with a ten second exposure time. Integration of these frames followed by reflection indexing and least squares refinement produced a crystal orientation matrix for the triclinic lattice.

Data collection consisted of the measurement of a total of 1650 frames in five different runs covering a hemisphere of data. All 1650 crystallographic raw data frames were read by program SAINT (version 5/6.0)[1] and integrated using 3D profiling algorithms. The resulting data were reduced to produce a total of 27825 reflections and their intensities and estimated standard deviations. An absorption correction was applied using the SADABS routine available in SAINT. The data were corrected for Lorentz and polarization effects as well as any crystal decay. The unit cell parameters, based upon the refinement of 8512 reflections, are a=13.9403(8) Å, b=15.4456(8) Å, c=18.8204(11) Å, α=91.580(1)°, β=107.242(1)°, γ=93.358(1)°, and V=3859.3(4) Å$^3$. Data preparation was carried out by using the program XPREP,[1] which gave 17246 unique reflections (R$_{int}$=2.84%) with indices −17≦h≦18, −20≦k≦19, −21≦1≦24. The space group was determined to be P(−1) (No. 2).

The structure was solved by a combination of direct methods and Fourier methods with the use of SHELXTL6.1. There are two different molecules in the crystallographic asymmetric unit. One compound is the five-coordinate complex [(C$_6$Me$_5$)NCH$_2$CH$_2$NHCH$_2$CH$_2$N(C$_6$Me$_5$)]Zr(OC$_6$F$_5$)$_2$ and the other is its six-coordinate dimethylamine adduct [(C$_6$Me$_5$)NCH$_2$CH$_2$NHCH$_2$CH$_2$N(C$_6$Me$_5$)]Zr(Oc$_6$F$_5$)$_2$(NMe$_2$H). The positions for the hydrogen atoms bound to N(2), N(5), and N(7) were refined with their isotropic temperature factors set at 1.2 times that of the respective nitrogen atom. Idealized positions for the remaining hydrogen atoms were included as fixed contributions using a riding model with isotropic temperature factors set at 1.2 (aromatic protons) or 1.5 (methyl protons) times that of the adjacent carbon atom. The positions of the methyl hydrogens were optimized by a rigid rotating group refinement with idealized tetrahedral angles. Full-matrix least-squares refinement, based upon the minimization of εw$_i$ |F$_o$$^2$−F$_c$$^2$|$^2$, with w$_i$$^{−1}$=[σ$^2$ (F$_o$$^2$)+(0.0601

P)² +0.1887 P], where P=(Max(F$_o^2$, 0)+2 F$_c^2$)/3, converged to give final discrepancy indices of R1=0.0446, wR2=0.1157 for 12456 reflections with I>2σ(I). The goodness of fit (GOF) value was 1.075.

A correction for secondary extinction was not applied. The maximum and minimum residual electron density peaks in the final difference Fourier map were 0.567 and −0.833 e/Å³, respectively. The linear absorption coefficient, atomic scattering factors and anomalous dispersion corrections were calculated from values from the International Tables for X-ray Crystallography.

Figure 2:
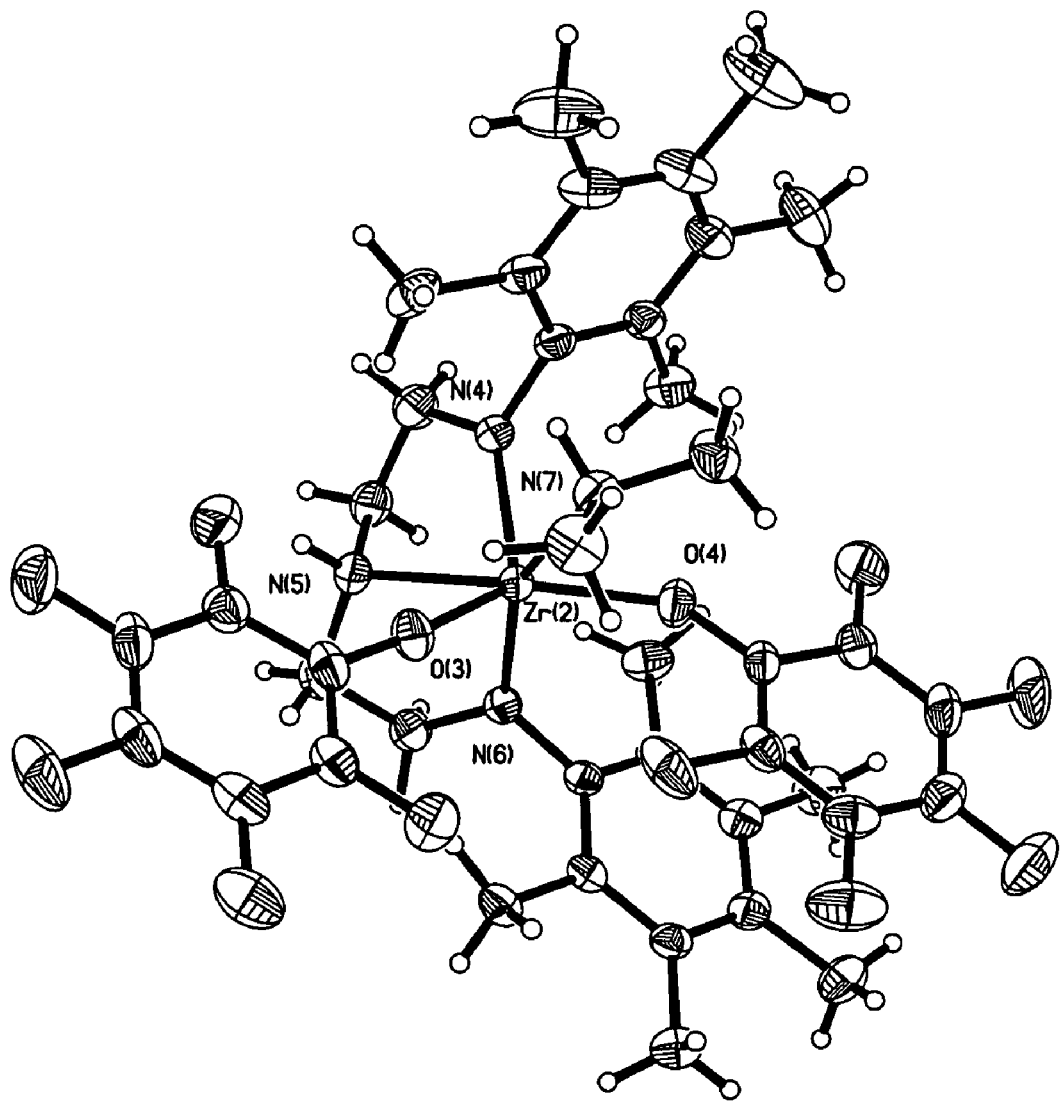
FIG. 2 shows a perspective drawing of the solid-state structure for a [(C$_6$Me$_5$)NCH$_2$CH$_2$NHCH$_2$CH$_2$N(C$_6$Me$_5$)]Zr (OC$_6$F$_5$)$_2$(NMe$_2$H) molecule. Non-hydrogen atoms are represented by 30% probability thermal vibration ellipsoids and hydrogen atoms are represented by arbitrarily-small spheres which are in no way representative of their true thermal motion.

FIG. 1 shows an ORTEP of [(C$_6$Me$_5$)NCH$_2$CH$_2$NHCH$_2$CH$_2$N(C$_6$Me$_5$)]Zr(OC$_6$F$_5$)$_2$. FIG. 2 shows an ORTEP of [(C$_6$Me$_5$)NCH$_2$CH$_2$NHCH$_2$CH$_2$N(C$_6$Me$_5$)]Zr(OC$_6$F$_5$)$_2$(NMe$_2$H). Atomic Coordinates for Nonhydrogen Atoms and equivalent isotropic displacement parameters are listed in Table 1. Table 2 lists the interatomic distances [Å] and bond angles [°]. Table 3 lists the anisotropic displacement parameters [A²×10³]. Table 4 lists the hydrogen atom coordinates (×10⁴) and isotropic displacement parameters.

TABLE 1

Atomic coordinates [×10⁴] and equivalent isotropic displacement parameters [A² × 10³]. U(eq) is defined as one third of the trace of the orthogonalized U$_{ij}$ tensor.

|  | x | y | z | U(eq) |
|---|---|---|---|---|
| Zr(1) | 3424(1) | 9082(1) | 1698(1) | 36(1) |
| O(1) | 4091(2) | 7987(1) | 2009(1) | 48(1) |
| O(2) | 1969(2) | 8740(1) | 1175(1) | 58(1) |
| N(1) | 3616(2) | 9800(1) | 2661(1) | 41(1) |
| N(2) | 3150(2) | 10551(1) | 1399(1) | 50(1) |
| N(3) | 4241(2) | 9425(1) | 999(1) | 43(1) |
| F(1) | 3014(1) | 6846(1) | 896(1) | 72(1) |
| F(2) | 3759(2) | 5359(1) | 607(2) | 112(1) |
| F(3) | 5645(2) | 4983(1) | 1409(2) | 123(1) |
| F(4) | 6757(2) | 6115(1) | 2496(2) | 109(1) |
| F(5) | 6014(2) | 7597(1) | 2804(1) | 83(1) |
| F(6) | 706(2) | 10059(1) | 1059(1) | 97(1) |
| F(7) | −1287(2) | 9785(2) | 351(2) | 104(1) |
| F(8) | −2069(1) | 8185(1) | −258(1) | 81(1) |
| F(9) | −843(2) | 6862(1) | −153(2) | 97(1) |
| F(10) | 1142(2) | 7143(1) | 519(2) | 97(1) |
| C(1) | 3529(3) | 10738(2) | 2733(2) | 54(1) |
| C(2) | 2879(3) | 11017(2) | 1994(2) | 58(1) |
| C(3) | 4078(3) | 10920(2) | 1267(2) | 58(1) |
| C(4) | 4357(3) | 10307(2) | 742(2) | 60(1) |
| C(5) | 3841(2) | 9377(2) | 3358(1) | 42(1) |
| C(6) | 3047(2) | 9030(2) | 3595(2) | 49(1) |
| C(7) | 3280(3) | 8617(2) | 4279(2) | 57(1) |
| C(8) | 4267(3) | 8554(2) | 4702(2) | 58(1) |
| C(9) | 5052(2) | 8909(2) | 4465(2) | 52(1) |
| C(10) | 4845(2) | 9329(2) | 3788(2) | 43(1) |
| C(11) | 1971(2) | 9100(2) | 3135(2) | 66(1) |
| C(12) | 2407(3) | 8244(3) | 4539(2) | 90(1) |
| C(13) | 4509(3) | 8091(3) | 5429(2) | 84(1) |
| C(14) | 6140(3) | 8860(2) | 4922(2) | 74(1) |
| C(15) | 5684(2) | 9715(2) | 3528(1) | 55(1) |
| C(16) | 4707(2) | 8777(2) | 681(1) | 39(1) |
| C(17) | 5719(2) | 8627(2) | 1036(1) | 44(1) |
| C(18) | 6148(2) | 7940(2) | 778(2) | 50(1) |
| C(19) | 5595(2) | 7433(2) | 149(2) | 51(1) |
| C(20) | 4615(2) | 7616(2) | −226(2) | 49(1) |
| C(21) | 4159(2) | 8284(2) | 41(2) | 43(1) |
| C(22) | 6321(2) | 9208(2) | 1690(2) | 65(1) |
| C(23) | 7226(3) | 7761(3) | 1201(2) | 79(1) |
| C(24) | 6054(3) | 6670(2) | −121(2) | 79(1) |
| C(25) | 4021(3) | 7101(3) | −927(2) | 85(1) |
| C(26) | 3082(2) | 8478(2) | −356(2) | 62(1) |
| C(27) | 4472(2) | 7255(2) | 1866(2) | 44(1) |
| C(28) | 3937(2) | 6665(2) | 1308(2) | 52(1) |
| C(29) | 4307(3) | 5906(2) | 1155(2) | 66(1) |
| C(30) | 5267(3) | 5725(2) | 1556(2) | 74(1) |

TABLE 1-continued

Atomic coordinates [×10⁴] and equivalent isotropic displacement parameters [A² × 10³]. U(eq) is defined as one third of the trace of the orthogonalized U$_{ij}$ tensor.

|  | x | y | z | U(eq) |
|---|---|---|---|---|
| C(31) | 5815(3) | 6291(2) | 2105(2) | 69(1) |
| C(32) | 5428(2) | 7044(2) | 2262(2) | 56(1) |
| C(33) | 989(2) | 8598(2) | 838(2) | 51(1) |
| C(34) | 331(3) | 9256(2) | 776(2) | 64(1) |
| C(35) | −682(3) | 9115(3) | 421(2) | 70(1) |
| C(36) | −1076(2) | 8313(2) | 108(2) | 62(1) |
| C(37) | −457(2) | 7656(2) | 168(2) | 62(1) |
| C(38) | 556(2) | 7799(2) | 523(2) | 60(1) |
| Zr(2) | 438(1) | 4767(1) | 2678(1) | 37(1) |
| O(3) | −180(2) | 5756(1) | 3075(1) | 56(1) |
| O(4) | 875(2) | 3616(1) | 3126(1) | 60(1) |
| N(4) | 1540(2) | 5085(1) | 2171(1) | 44(1) |
| N(5) | −282(2) | 5492(2) | 1560(1) | 50(1) |
| N(6) | −861(2) | 4049(1) | 2025(1) | 44(1) |
| N(7) | 1751(2) | 5209(2) | 3908(1) | 51(1) |
| F(11) | −1329(2) | 5685(1) | 4037(1) | 73(1) |
| F(12) | −2241(2) | 7082(2) | 4317(1) | 85(1) |
| F(13) | −1995(2) | 8607(1) | 3695(1) | 96(1) |
| F(14) | −838(2) | 8703(1) | 2750(1) | 94(1) |
| F(15) | 27(2) | 7299(1) | 2432(1) | 77(1) |
| F(16) | −270(2) | 3864(1) | 4041(1) | 84(1) |
| F(17) | −657(2) | 2578(1) | 4881(1) | 100(1) |
| F(18) | 180(2) | 1040(2) | 4879(1) | 105(1) |
| F(19) | 1411(2) | 806(1) | 4025(1) | 101(1) |
| F(20) | 1769(2) | 2066(1) | 3163(1) | 83(1) |
| C(39) | 1346(3) | 5377(2) | 1404(2) | 63(1) |
| C(40) | 241(2) | 5226(1) | 1030(2) | 59(1) |
| C(41) | −1378(2) | 5305(2) | 1306(2) | 61(1) |
| C(42) | −1584(2) | 4343(2) | 1347(2) | 61(1) |
| C(43) | 2607(2) | 5087(2) | 2532(2) | 44(1) |
| C(44) | 3096(2) | 4331(2) | 2479(2) | 47(1) |
| C(45) | 4105(2) | 4302(2) | 2870(2) | 60(1) |
| C(46) | 4627(2) | 5025(3) | 3315(2) | 70(1) |
| C(47) | 4151(3) | 5794(2) | 3331(2) | 65(1) |
| C(48) | 3147(2) | 5828(2) | 2928(2) | 52(1) |
| C(49) | 2519(2) | 3558(2) | 2003(2) | 62(1) |
| C(50) | 4621(2) | 3472(2) | 2822(3) | 95(1) |
| C(51) | 5734(3) | 4975(4) | 3779(3) | 126(2) |
| C(52) | 4708(3) | 6585(3) | 3809(3) | 109(2) |
| C(53) | 2621(3) | 6667(2) | 2916(2) | 70(1) |
| C(54) | −1215(2) | 3220(2) | 2221(1) | 40(1) |
| C(55) | −1898(2) | 3185(2) | 2632(2) | 43(1) |
| C(56) | −2177(2) | 2383(2) | 2873(2) | 45(1) |
| C(57) | −1756(2) | 1632(2) | 2721(2) | 48(1) |
| C(58) | −1110(2) | 1661(2) | 2281(2) | 48(1) |
| C(59) | −851(2) | 2450(2) | 2013(2) | 45(1) |
| C(60) | −2326(2) | 4004(2) | 2824(2) | 57(1) |
| C(61) | −2917(3) | 2347(2) | 3317(2) | 69(1) |
| C(62) | −1998(3) | 780(2) | 3046(2) | 70(1) |
| C(63) | −677(3) | 843(2) | 2091(2) | 75(1) |
| C(64) | −178(3) | 2489(2) | 1517(2) | 62(1) |
| C(65) | −618(2) | 6442(2) | 3223(2) | 50(1) |
| C(66) | −1202(2) | 6424(2) | 3708(2) | 53(1) |
| C(67) | −1668(2) | 7141(2) | 3861(2) | 61(1) |
| C(68) | −1551(3) | 7909(2) | 3542(2) | 65(1) |
| C(69) | −974(3) | 7954(2) | 3075(2) | 65(1) |
| C(70) | −523(2) | 7236(2) | 2913(2) | 56(1) |
| C(71) | 732(2) | 2999(2) | 3563(2) | 45(1) |
| C(72) | 1172(2) | 2210(2) | 3589(2) | 51(1) |
| C(73) | 990(3) | 1568(2) | 4026(2) | 61(1) |
| C(74) | 371(3) | 1671(2) | 4459(2) | 64(1) |
| C(75) | −53(2) | 2452(2) | 4460(2) | 63(1) |
| C(76) | 141(2) | 3093(2) | 4027(2) | 52(1) |
| C(77) | 2489(2) | 4572(2) | 4241(2) | 66(1) |
| C(78) | 1420(3) | 5634(2) | 4496(2) | 72(1) |

TABLE 2

Interatomic distances [Å] and bond angles [°].

| | | | |
|---|---|---|---|
| Zr(1)—O(1) | 1.9951(16) | Zr(1)—O(2) | 2.006(2) |
| Zr(1)—N(1) | 2.039(2) | Zr(1)—N(3) | 2.040(2) |
| Zr(1)—N(2) | 2.377(2) | O(1)—C(27) | 1.332(3) |
| O(2)—C(33) | 1.327(3) | N(1)—C(5) | 1.439(3) |
| N(1)—C(1) | 1.466(3) | N(2)—C(2) | 1.468(4) |
| N(2)—C(3) | 1.474(4) | N(3)—C(16) | 1.434(3) |
| N(3)—C(4) | 1.474(3) | F(1)—C(28) | 1.340(3) |
| F(2)—C(29) | 1.331(4) | F(3)—C(30) | 1.346(3) |
| F(4)—C(31) | 1.349(4) | F(5)—C(32) | 1.347(3) |
| F(6)—C(34) | 1.347(4) | F(7)—C(35) | 1.357(4) |
| F(8)—C(36) | 1.351(4) | F(9)—C(37) | 1.359(4) |
| F(10)—C(38) | 1.340(4) | C(1)—C(2) | 1.508(4) |
| C(3)—C(4) | 1.498(4) | C(5)—C(6) | 1.397(4) |
| C(5)—C(10) | 1.401(4) | (6)-C(7) | 1.411(4) |
| C(6)—C(11) | 1.504(4) | (7)-C(8) | 1.381(5) |
| C(7)—C(12) | 1.530(5) | (8)-C(9) | 1.390(5) |
| C(8)—C(13) | 1.519(4) | (9)-C(10) | 1.406(4) |
| C(9)—C(14) | 1.513(4) | (10)-C(15) | 1.495(4) |
| C(16)—C(21) | 1.396(4) | (16)-C(17) | 1.407(4) |
| C(17)—C(18) | 1.392(4) | (17)-C(22) | 1.505(4) |
| C(18)—C(19) | 1.396(4) | C(18)—C(23) | 1.523(4) |
| C(19)—C(20) | 1.389(4) | C(19)—C(24) | 1.517(4) |
| C(20)—C(21) | 1.400(4) | C(20)—C(25) | 1.508(4) |
| C(21)—C(26) | 1.517(4) | C(27)—C(28) | 1.376(4) |
| C(27)—C(32) | 1.382(4) | C(28)—C(29) | 1.365(4) |
| C(29)—C(30) | 1.377(5) | C(30)—C(31) | 1.347(5) |
| C(31)—C(32) | 1.372(4) | C(33)—C(38) | 1.377(4) |
| C(33)—C(34) | 1.393(4) | C(34)—C(35) | 1.374(5) |
| C(35)—C(36) | 1.369(5) | C(36)—C(37) | 1.356(4) |
| C(37)—C(38) | 1.374(4) | Zr(2)—O(3) | 2.0274(18) |
| Zr(2)—O(4) | 2.0371(17) | Zr(2)—N(4) | 2.078(2) |
| Zr(2)—N(6) | 2.095(2) | Zr(2)—N(5) | 2.387(2) |
| Zr(2)—N(7) | 2.537(2) | O(3)—C(65) | 1.316(3) |
| O(4)—C(71) | 1.319(3) | N(4)—C(43) | 1.440(3) |
| N(4)—C(39) | 1.477(3) | N(5)—C(40) | 1.463(4) |
| N(5)—C(41) | 1.467(4) | N(6)—C(54) | 1.442(3) |
| N(6)—C(42) | 1.473(3) | N(7)—C(78) | 1.471(4) |
| N(7)—C(77) | 1.480(4) | F(11)—C(66) | 1.341(3) |
| F(12)—C(67) | 1.336(4) | F(13)—C(68) | 1.340(3) |
| F(14)—C(69) | 1.354(4) | F(15)—C(70) | 1.351(4) |
| F(16)—C(76) | 1.354(3) | F(17)—C(75) | 1.333(4) |
| F(18)—C(74) | 1.336(3) | F(19)—C(73) | 1.346(3) |
| F(20)—C(72) | 1.339(3) | C(39)—C(40) | 1.493(4) |
| C(41)—C(42) | 1.505(4) | C(43)—C(48) | 1.396(4) |
| C(43)—C(44) | 1.402(4) | C(44)—C(45) | 1.385(4) |
| C(44)—C(49) | 1.509(4) | C(45)—C(46) | 1.403(5) |
| C(45)—C(50) | 1.519(4) | C(46)—C(47) | 1.397(5) |
| C(46)—C(51) | 1.539(5) | C(47)—C(48) | 1.385(4) |
| C(47)—C(52) | 1.524(5) | C(48)—C(53) | 1.523(4) |
| C(54)—C(55) | 1.393(4) | C(54)—C(59) | 1.409(4) |
| C(55)—C(56) | 1.404(4) | C(55)—C(60) | 1.509(4) |
| C(56)—C(57) | 1.391(4) | C(56)—C(61) | 1.506(4) |
| C(57)—C(58) | 1.392(4) | (57)-C(62) | 1.527(4) |
| C(58)—C(59) | 1.400(4) | (58)-C(63) | 1.510(4) |
| C(59)—C(64) | 1.507(4) | (65)-C(70) | 1.388(4) |
| C(65)—C(66) | 1.391(4) | (66)-C(67) | 1.383(4) |
| C(67)—C(68) | 1.367(5) | (68)-C(69) | 1.357(5) |
| C(69)—C(70) | 1.375(4) | (71)-C(76) | 1.375(4) |
| C(71)—C(72) | 1.392(3) | (72)-C(73) | 1.364(4) |
| C(73)—C(74) | 1.364(5) | C(74)—C(75) | 1.375(5) |
| C(75)—C(76) | 1.366(4) | O(1)—Zr(1)—O(2) | 106.74(8) |
| O(1)—Zr(1)—N(1) | 105.34(8) | O(2)—Zr(1)—N(1) | 112.22(9) |
| O(1)—Zr(1)—N(3) | 96.10(8) | O(2)—Zr(1)—N(3) | 113.98(9) |
| N(1)—Zr(1)—N(3) | 119.81(9) | O(1)—Zr(1)—N(2) | 162.46(9) |
| O(2)—Zr(1)—N(2) | 90.12(9) | N(1)—Zr(1)—N(2) | 71.50(8) |
| N(3)—Zr(1)—N(2) | 72.02(9) | C(27)—O(1)—Zr(1) | 152.21(18) |
| C(33)—O(2)—Zr(1) | 174.2(2) | C(5)—N(1)—C(1) | 113.8(2) |
| C(5)—N(1)—Zr(1) | 119.56(15) | C(1)—N(1)—Zr(1) | 126.61(17) |
| C(2)—N(2)—C(3) | 113.7(3) | C(2)—N(2)—Zr(1) | 110.47(18) |
| C(3)—N(2)—Zr(1) | 106.46(16) | C(16)—N(3)—C(4) | 114.6(2) |
| C(16)—N(3)—Zr(1) | 120.15(15) | C(4)—N(3)—Zr(1) | 125.12(18) |
| N(1)—C(1)—C(2) | 107.5(2) | N(2)—C(2)—C(1) | 108.4(2) |
| N(2)—C(3)—C(4) | 108.1(3) | N(3)—C(4)—C(3) | 106.9(2) |
| C(6)—C(5)—C(10) | 121.3(2) | C(6)—C(5)—N(1) | 118.9(2) |

TABLE 2-continued

Interatomic distances [Å] and bond angles [°].

| | | | |
|---|---|---|---|
| C(10)—C(5)—N(1) | 119.8(2) | C(5)—C(6)—C(7) | 118.2(3) |
| C(5)—C(6)—C(11) | 120.8(3) | C(7)—C(6)—C(11) | 121.0(3) |
| C(8)—C(7)—C(6) | 121.0(3) | C(8)—C(7)—C(12) | 121.0(3) |
| C(6)—C(7)—C(12) | 118.0(3) | C(7)—C(8)—C(9) | 120.4(3) |
| C(7)—C(8)—C(13) | 120.5(3) | C(9)—C(8)—C(13) | 119.1(3) |
| C(8)—C(9)—C(10) | 120.0(3) | C(8)—C(9)—C(14) | 121.5(3) |
| C(10)—C(9)—C(14) | 118.5(3) | C(5)—C(10)—C(9) | 119.1(3) |
| C(5)—C(10)—C(15) | 120.4(2) | C(9)—C(10)—C(15) | 120.5(3) |
| C(21)—C(16)—C(17) | 120.3(2) | C(21)—C(16)—N(3) | 120.7(2) |
| C(17)—C(16)—N(3) | 118.9(2) | C(18)—C(17)—C(16) | 119.4(2) |
| C(18)—C(17)—C(22) | 120.9(3) | C(16)—C(17)—C(22) | 119.6(3) |
| C(17)—C(18)—C(19) | 120.2(3) | C(17)—C(18)—C(23) | 118.3(3) |
| C(19)—C(18)—C(23) | 121.5(3) | C(20)—C(19)—C(18) | 120.1(3) |
| C(20)—C(19)—C(24) | 119.7(3) | C(18)—C(19)—C(24) | 120.2(3) |
| C(19)—C(20)—C(21) | 120.4(3) | C(19)—C(20)—C(25) | 120.9(3) |
| C(21)—C(20)—C(25) | 118.7(3) | C(16)—C(21)—C(20) | 119.3(2) |
| C(16)—C(21)—C(26) | 119.8(3) | C(20)—C(21)—C(26) | 120.8(3) |
| O(1)—C(27)—C(28) | 121.6(2) | O(1)—C(27)—C(32) | 122.3(3) |
| C(28)—C(27)—C(32) | 116.1(2) | F(1)—C(28)—C(29) | 118.7(3) |
| F(1)—C(28)—C(27) | 118.5(2) | C(29)—C(28)—C(27) | 122.7(3) |
| F(2)—C(29)—C(28) | 120.4(3) | F(2)—C(29)—C(30) | 120.2(3) |
| C(28)—C(29)—C(30) | 119.4(3) | F(3)—C(30)—C(31) | 120.5(3) |
| F(3)—C(30)—C(29) | 120.1(3) | C(31)—C(30)—C(29) | 119.4(3) |
| C(30)—C(31)—F(4) | 119.4(3) | C(30)—C(31)—C(32) | 120.6(3) |
| F(4)—C(31)—C(32) | 119.9(3) | F(5)—C(32)—C(31) | 118.3(3) |
| F(5)—C(32)—C(27) | 119.9(3) | C(31)—C(32)—C(27) | 121.7(3) |
| O(2)—C(33)—C(38) | 122.6(3) | O(2)—C(33)—C(34) | 121.7(3) |
| C(38)—C(33)—C(34) | 115.7(3) | F(6)—C(34)—C(35) | 119.2(3) |
| F(6)—C(34)—C(33) | 118.9(3) | C(35)—C(34)—C(33) | 121.9(3) |
| F(7)—C(35)—C(36) | 119.9(3) | F(7)—C(35)—C(34) | 119.8(4) |
| C(36)—C(35)—C(34) | 120.3(3) | F(8)—C(36)—C(37) | 120.9(3) |
| F(8)—C(36)—C(35) | 120.0(3) | C(37)—C(36)—C(35) | 119.2(3) |
| C(36)—C(37)—F(9) | 119.3(3) | C(36)—C(37)—C(38) | 120.4(3) |
| F(9)—C(37)—C(38) | 120.3(3) | F(10)—C(38)—C(37) | 117.7(3) |
| F(10)—C(38)—C(33) | 119.6(3) | C(37)—C(38)—C(33) | 122.5(3) |
| O(3)—Zr(2)—O(4) | 130.31(9) | O(3)—Zr(2)—N(4) | 117.59(9) |
| O(4)—Zr(2)—N(4) | 101.88(9) | O(3)—Zr(2)—N(6) | 100.70(9) |
| O(4)—Zr(2)—N(6) | 85.67(8) | N(4)—Zr(2)—N(6) | 116.89(9) |
| O(3)—Zr(2)—N(5) | 79.28(8) | O(4)—Zr(2)—N(5) | 145.83(9) |
| N(4)—Zr(2)—N(5) | 70.28(8) | N(6)—Zr(2)—N(5) | 70.22(8) |
| O(3)—Zr(2)—N(7) | 77.11(8) | O(4)—Zr(2)—N(7) | 76.07(8) |
| N(4)—Zr(2)—N(7) | 86.99(9) | N(6)—Zr(2)—N(7) | 152.73(8) |
| N(5)—Zr(2)—N(7) | 134.24(8) | C(65)—O(3)—Zr(2) | 170.69(19) |
| C(71)—O(4)—Zr(2) | 146.6(2) | C(43)—N(4)—C(39) | 110.4(2) |
| C(43)—N(4)—Zr(2) | 124.57(16) | C(39)—N(4)—Zr(2) | 125.03(19) |
| C(40)—N(5)—C(41) | 114.9(3) | C(40)—N(5)—Zr(2) | 106.61(16) |
| C(41)—N(5)—Zr(2) | 110.03(17) | C(54)—N(6)—C(42) | 110.5(2) |
| C(54)—N(6)—Zr(2) | 123.71(15) | C(42)—N(6)—Zr(2) | 125.55(17) |
| C(78)—N(7)—C(77) | 109.5(3) | C(78)—N(7)—Zr(2) | 118.3(2) |
| C(77)—N(7)—Zr(2) | 117.41(19) | N(4)—C(39)—C(40) | 107.1(2) |
| N(5)—C(40)—C(39) | 107.8(3) | N(5)—C(41)—C(42) | 107.7(2) |
| N(6)—C(42)—C(41) | 108.5(2) | C(48)—C(43)—C(44) | 120.5(3) |
| C(48)—C(43)—N(4) | 120.7(2) | C(44)—C(43)—N(4) | 118.8(2) |
| C(45)—C(44)—C(43) | 119.4(3) | C(45)—C(44)—C(49) | 120.8(3) |
| C(43)—C(44)—C(49) | 119.9(3) | C(44)—C(45)—C(46) | 119.9(3) |
| C(44)—C(45)—C(50) | 118.9(3) | C(46)—C(45)—C(50) | 121.2(3) |
| C(47)—C(46)—C(45) | 120.4(3) | C(47)—C(46)—C(51) | 119.9(4) |
| C(45)—C(46)—C(51) | 119.8(4) | C(48)—C(47)—C(46) | 119.6(3) |
| C(48)—C(47)—C(52) | 119.4(3) | C(46)—C(47)—C(52) | 121.0(4) |
| C(47)—C(48)—C(43) | 119.9(3) | C(47)—C(48)—C(53) | 120.5(3) |
| C(43)—C(48)—C(53) | 119.5(3) | C(55)—C(54)—C(59) | 120.3(2) |
| C(55)—C(54)—N(6) | 119.8(2) | C(59)—C(54)—N(6) | 120.0(2) |
| C(54)—C(55)—C(56) | 119.4(2) | C(54)—C(55)—C(60) | 120.3(2) |
| C(56)—C(55)—C(60) | 120.2(3) | C(57)—C(56)—C(55) | 120.4(3) |
| C(57)—C(56)—C(61) | 120.2(3) | C(55)—C(56)—C(61) | 119.4(3) |
| C(56)—C(57)—C(58) | 120.0(2) | C(56)—C(57)—C(62) | 119.6(3) |
| C(58)—C(57)—C(62) | 120.4(3) | C(57)—C(58)—C(59) | 120.3(2) |
| C(57)—C(58)—C(63) | 120.4(3) | C(59)—C(58)—C(63) | 119.3(3) |
| C(58)—C(59)—C(54) | 119.3(3) | C(58)—C(59)—C(64) | 121.0(3) |
| C(54)—C(59)—C(64) | 119.8(2) | O(3)—C(65)—C(70) | 122.6(3) |
| O(3)—C(65)—C(66) | 122.2(3) | C(70)—C(65)—C(66) | 115.2(3) |
| F(11)—C(66)—C(67) | 118.2(3) | F(11)—C(66)—C(65) | 119.4(2) |
| C(67)—C(66)—C(65) | 122.4(3) | F(12)—C(67)—C(68) | 120.0(3) |
| F(12)—C(67)—C(66) | 119.9(3) | C(68)—C(67)—C(66) | 120.1(3) |
| F(13)—C(68)—C(69) | 120.8(3) | F(13)—C(68)—C(67) | 120.2(4) |

TABLE 2-continued

Interatomic distances [Å] and bond angles [°].

| | | | | |
|---|---|---|---|---|
| C(69)—C(68)—C(67) | 119.0(3) | F(14)—C(69)—C(68) | 120.8(3) |
| F(14)—C(69)—C(70) | 118.4(4) | C(68)—C(69)—C(70) | 120.8(3) |
| F(15)—C(70)—C(69) | 119.2(3) | F(15)—C(70)—C(65) | 118.4(3) |
| C(69)—C(70)—C(65) | 122.4(3) | O(4)—C(71)—C(76) | 122.3(2) |
| O(4)—C(71)—C(72) | 122.3(3) | C(76)—C(71)—C(72) | 115.4(2) |
| F(20)—C(72)—C(73) | 118.9(3) | F(20)—C(72)—C(71) | 119.5(3) |
| C(73)—C(72)—C(71) | 121.6(3) | F(19)—C(73)—C(72) | 120.0(3) |
| F(19)—C(73)—C(74) | 118.4(3) | C(72)—C(73)—C(74) | 121.5(3) |
| F(18)—C(74)—C(73) | 121.8(3) | F(18)—C(74)—C(75) | 120.0(4) |
| C(73)—C(74)—C(75) | 118.2(3) | F(17)—C(75)—C(76) | 120.3(3) |
| F(17)—C(75)—C(74) | 119.9(3) | C(76)—C(75)—C(74) | 119.7(3) |
| F(16)—C(76)—C(75) | 119.1(3) | F(16)—C(76)—C(71) | 117.4(3) |
| C(75)—C(76)—C(71) | 123.4(3) | | |

TABLE 3

Anisotropic displacement parameters [Å$^2$ × 10$^3$]. The anisotropic displacement factor exponent takes the form: $-2\pi^2[(ha^*)^2 U_{11} + \ldots + 2hka^* b^* U_{12}]$.

| | $U_{11}$ | $U_{22}$ | $U_{33}$ | $U_{23}$ | $U_{13}$ | $U_{12}$ |
|---|---|---|---|---|---|---|
| Zr(1) | 38(1) | 32(1) | 40(1) | −1(1) | 12(1) | 6(1) |
| O(1) | 56(1) | 34(1) | 60(1) | 7(1) | 28(1) | 11(1) |
| O(2) | 39(1) | 66(1) | 64(1) | −3(1) | 9(1) | 4(1) |
| N(1) | 46(1) | 37(1) | 43(1) | −2(1) | 14(1) | 6(1) |
| N(2) | 62(2) | 39(1) | 47(1) | 2(1) | 10(1) | 14(1) |
| N(3) | 50(1) | 36(1) | 46(1) | 3(1) | 19(1) | 1(1) |
| F(1) | 48(1) | 68(1) | 90(1) | −2(1) | 7(1) | 13(1) |
| F(2) | 94(2) | 75(1) | 133(2) | −54(1) | −16(2) | 17(1) |
| F(3) | 109(2) | 68(1) | 165(3) | −40(1) | −6(2) | 49(1) |
| F(4) | 73(2) | 85(2) | 139(2) | −16(1) | −18(2) | 40(1) |
| F(5) | 75(1) | 62(1) | 90(2) | −22(1) | −7(1) | 9(1) |
| F(6) | 65(1) | 92(2) | 120(2) | −46(1) | 11(1) | 14(1) |
| F(7) | 62(1) | 112(2) | 128(2) | −31(2) | 13(1) | 35(1) |
| F(8) | 40(1) | 103(2) | 88(2) | 25(1) | 0(1) | 3(1) |
| F(9) | 62(1) | 62(1) | 139(2) | 20(1) | −11(1) | −9(1) |
| F(10) | 56(1) | 55(1) | 157(2) | 17(1) | −7(1) | 9(1) |
| C(1) | 71(2) | 39(1) | 53(2) | −7(1) | 19(2) | 12(1) |
| C(2) | 67(2) | 39(1) | 68(2) | −3(1) | 18(2) | 17(1) |
| C(3) | 79(2) | 33(1) | 66(2) | 7(1) | 26(2) | 4(1) |
| C(4) | 81(2) | 44(2) | 62(2) | 10(1) | 31(2) | 5(2) |
| C(5) | 51(2) | 38(1) | 39(1) | −8(1) | 18(1) | 4(1) |
| C(6) | 55(2) | 48(2) | 50(2) | −12(1) | 26(1) | −1(1) |
| C(7) | 70(2) | 54(2) | 54(2) | −8(1) | 35(2) | −7(2) |
| C(8) | 85(3) | 50(2) | 45(2) | −4(1) | 30(2) | 2(2) |
| C(9) | 63(2) | 48(2) | 43(2) | −7(1) | 15(2) | 5(1) |
| C(10) | 50(2) | 38(1) | 41(1) | −7(1) | 15(1) | 1(1) |
| C(11) | 53(2) | 73(2) | 78(2) | −12(2) | 31(2) | −1(2) |
| C(12) | 105(3) | 99(3) | 82(3) | 0(2) | 57(3) | −21(2) |
| C(13) | 116(4) | 91(3) | 51(2) | 11(2) | 33(2) | 5(2) |
| C(14) | 74(3) | 91(3) | 51(2) | 6(2) | 6(2) | 13(2) |
| C(15) | 46(2) | 65(2) | 55(2) | 1(1) | 16(2) | 1(1) |
| C(16) | 41(2) | 41(1) | 36(1) | 3(1) | 15(1) | 0(1) |
| C(17) | 43(2) | 53(2) | 36(1) | −4(1) | 13(1) | −3(1) |
| C(18) | 42(2) | 61(2) | 47(2) | 4(1) | 14(1) | 8(1) |
| C(19) | 53(2) | 46(2) | 57(2) | −3(1) | 22(2) | 2(1) |
| C(20) | 50(2) | 46(2) | 49(2) | −10(1) | 13(1) | −7(1) |
| C(21) | 40(2) | 46(1) | 43(2) | 2(1) | 10(1) | −4(1) |
| C(22) | 50(2) | 88(2) | 51(2) | −16(2) | 11(2) | −8(2) |
| C(23) | 51(2) | 115(3) | 71(2) | 0(2) | 14(2) | 25(2) |
| C(24) | 74(3) | 67(2) | 101(3) | −19(2) | 35(2) | 13(2) |
| C(25) | 75(3) | 83(3) | 87(3) | −44(2) | 15(2) | −11(2) |
| C(26) | 49(2) | 80(2) | 51(2) | −2(2) | 3(2) | 7(2) |
| C(27) | 49(2) | 33(1) | 52(2) | 5(1) | 20(1) | 8(1) |
| C(28) | 43(2) | 47(2) | 65(2) | 4(1) | 13(2) | 9(1) |
| C(29) | 59(2) | 49(2) | 79(2) | −19(2) | 6(2) | 6(2) |
| C(30) | 71(2) | 44(2) | 98(3) | −14(2) | 9(2) | 24(2) |
| C(31) | 54(2) | 52(2) | 87(2) | −2(2) | −1(2) | 19(2) |
| C(32) | 56(2) | 41(2) | 65(2) | −5(1) | 9(2) | 7(1) |
| C(33) | 38(2) | 68(2) | 47(2) | 5(1) | 9(1) | 6(1) |
| C(34) | 54(2) | 71(2) | 65(2) | −16(2) | 18(2) | 5(2) |
| C(35) | 44(2) | 92(3) | 73(2) | −1(2) | 15(2) | 24(2) |
| C(36) | 39(2) | 80(2) | 63(2) | 16(2) | 8(2) | 2(2) |
| C(37) | 46(2) | 58(2) | 72(2) | 18(2) | 5(2) | −4(1) |
| C(38) | 44(2) | 55(2) | 75(2) | 21(2) | 7(2) | 3(1) |
| Zr(2) | 37(1) | 35(1) | 39(1) | 5(1) | 12(1) | 5(1) |
| O(3) | 63(1) | 47(1) | 61(1) | −1(1) | 20(1) | 18(1) |
| O(4) | 55(1) | 46(1) | 63(1) | 17(1) | −5(1) | −3(1) |
| N(4) | 41(1) | 47(1) | 46(1) | 10(1) | 17(1) | 3(1) |
| N(5) | 50(2) | 45(1) | 55(1) | 13(1) | 12(1) | 5(1) |
| N(6) | 39(1) | 48(1) | 42(1) | 9(1) | 9(1) | 2(1) |
| N(7) | 53(2) | 51(1) | 46(1) | 0(1) | 12(1) | −2(1) |
| F(11) | 94(2) | 63(1) | 70(1) | 4(1) | 36(1) | 9(1) |
| F(12) | 69(1) | 105(2) | 85(2) | −25(1) | 28(1) | 18(1) |
| F(13) | 80(2) | 71(1) | 124(2) | −30(1) | 8(1) | 39(1) |
| F(14) | 102(2) | 41(1) | 127(2) | 7(1) | 17(2) | 12(1) |
| F(15) | 80(1) | 54(1) | 103(2) | 8(1) | 36(1) | 4(1) |
| F(16) | 59(1) | 62(1) | 116(2) | −31(1) | 1(1) | 22(1) |
| F(17) | 78(2) | 148(2) | 80(2) | −27(1) | 41(1) | −18(2) |
| F(18) | 122(2) | 98(2) | 82(2) | 39(1) | 16(2) | −31(1) |
| F(19) | 122(2) | 43(1) | 126(2) | 15(1) | 14(2) | 33(1) |
| F(20) | 91(2) | 81(1) | 93(2) | 4(1) | 47(1) | 28(1) |
| C(39) | 64(2) | 78(2) | 55(2) | 21(2) | 26(2) | 7(2) |
| C(40) | 65(2) | 68(2) | 46(2) | 18(2) | 16(2) | 6(2) |
| C(41) | 50(2) | 68(2) | 60(2) | 23(2) | 4(2) | 11(2) |
| C(42) | 46(2) | 68(2) | 59(2) | 18(2) | 2(2) | 1(1) |
| C(43) | 44(2) | 43(1) | 49(2) | 4(1) | 21(1) | −1(1) |
| C(44) | 45(2) | 46(1) | 53(2) | 1(1) | 21(1) | 5(1) |
| C(45) | 49(2) | 71(2) | 66(2) | 0(2) | 22(2) | 14(2) |
| C(46) | 42(2) | 105(2) | 61(2) | −11(2) | 14(2) | 2(2) |
| C(47) | 52(2) | 76(2) | 67(2) | −22(2) | 25(2) | −15(2) |
| C(48) | 54(2) | 44(2) | 67(2) | −8(1) | 33(2) | −6(1) |
| C(49) | 66(2) | 49(2) | 76(2) | −14(2) | 34(2) | −2(2) |
| C(50) | 75(3) | 99(3) | 114(3) | 8(3) | 24(3) | 45(2) |
| C(51) | 58(3) | 199(6) | 100(4) | −31(4) | −4(3) | 19(3) |
| C(52) | 86(3) | 125(4) | 113(4) | −61(3) | 39(3) | −46(3) |
| C(53) | 92(3) | 40(2) | 95(3) | −4(2) | 56(2) | −6(2) |
| C(54) | 31(2) | 43(1) | 42(1) | −2(1) | 7(1) | −2(1) |
| C(55) | 34(1) | 50(2) | 43(1) | 0(1) | 9(1) | 5(1) |
| C(56) | 34(1) | 55(2) | 43(2) | 2(1) | 9(1) | −1(1) |
| C(57) | 43(2) | 46(2) | 49(2) | −2(1) | 7(1) | −7(1) |
| C(58) | 47(2) | 43(1) | 51(2) | −12(1) | 11(1) | −5(1) |
| C(59) | 38(2) | 52(2) | 44(2) | −8(1) | 12(1) | −4(1) |
| C(60) | 45(2) | 60(2) | 69(2) | 4(2) | 21(2) | 15(1) |
| C(61) | 61(2) | 76(2) | 78(2) | 12(2) | 34(2) | 4(2) |
| C(62) | 79(3) | 49(2) | 79(2) | 4(2) | 25(2) | −12(2) |
| C(63) | 87(3) | 47(2) | 97(3) | −17(2) | 39(2) | 1(2) |
| C(64) | 64(2) | 66(2) | 62(2) | −12(2) | 31(2) | −7(2) |
| C(65) | 45(2) | 42(1) | 56(2) | −4(1) | 3(1) | 13(1) |
| C(66) | 50(2) | 53(2) | 52(2) | −9(1) | 7(1) | 11(1) |
| C(67) | 42(2) | 73(2) | 61(2) | −18(2) | 7(2) | 11(2) |
| C(68) | 49(2) | 55(2) | 78(2) | −21(2) | −2(2) | 20(2) |
| C(69) | 60(2) | 39(2) | 80(2) | 1(2) | −3(2) | 11(1) |

TABLE 3-continued

Anisotropic displacement parameters [$A^2 \times 10^3$]. The anisotropic displacement factor exponent takes the form: $-2\pi^2[(ha^*)^2U_{11} + \ldots + 2hka^*b^*U_{12}]$.

| | $U_{11}$ | $U_{22}$ | $U_{33}$ | $U_{23}$ | $U_{13}$ | $U_{12}$ |
|---|---|---|---|---|---|---|
| C(70) | 50(2) | 49(2) | 67(2) | −2(1) | 14(2) | 6(1) |
| C(71) | 44(2) | 34(1) | 49(2) | 5(1) | 0(1) | 3(1) |
| C(72) | 54(2) | 46(2) | 54(2) | 1(1) | 16(2) | 13(1) |
| C(73) | 70(2) | 36(1) | 67(2) | 5(1) | 3(2) | 11(1) |
| C(74) | 66(2) | 60(2) | 55(2) | 12(2) | 5(2) | −14(2) |
| C(75) | 49(2) | 82(2) | 54(2) | −11(2) | 14(2) | −10(2) |
| C(76) | 42(2) | 45(2) | 61(2) | −10(1) | 2(1) | 7(1) |
| C(77) | 58(2) | 73(2) | 53(2) | 2(2) | −2(2) | 4(2) |
| C(78) | 81(3) | 80(2) | 52(2) | −17(2) | 17(2) | 3(2) |

TABLE 4

Hydrogen atom coordinates ($\times 10^4$) and isotropic displacement parameters ($A^2 \times 10^3$)

| | x | y | z | U(eq) |
|---|---|---|---|---|
| H(2) | 2630(20) | 10559(19) | 965(18) | 60 |
| H(1A) | 4196 | 11047 | 2863 | 65 |
| H(1B) | 3221 | 10868 | 3126 | 65 |
| H(2A) | 2166 | 10881 | 1948 | 70 |
| H(2B) | 2987 | 11645 | 1958 | 70 |
| H(3A) | 4622 | 10995 | 1738 | 70 |
| H(3B) | 3965 | 11489 | 1050 | 70 |
| H(4A) | 3914 | 10353 | 233 | 72 |
| H(4B) | 5054 | 10444 | 745 | 72 |
| H(11A) | 1687 | 8535 | 2905 | 99 |
| H(11B) | 1948 | 9511 | 2751 | 99 |
| H(11C) | 1585 | 9298 | 3453 | 99 |
| H(12A) | 2199 | 8688 | 4825 | 135 |
| H(12B) | 2622 | 7756 | 4847 | 135 |
| H(12C) | 1845 | 8050 | 4109 | 135 |
| H(13A) | 4297 | 8426 | 5792 | 126 |
| H(13B) | 5229 | 8033 | 5613 | 126 |
| H(13C) | 4157 | 7520 | 5345 | 126 |
| H(14A) | 6577 | 9130 | 4662 | 111 |
| H(14B) | 6286 | 8257 | 4996 | 111 |
| H(14C) | 6255 | 9163 | 5402 | 111 |
| H(15A) | 6105 | 10126 | 3909 | 83 |
| H(15B) | 5407 | 10013 | 3073 | 83 |
| H(15C) | 6085 | 9258 | 3434 | 83 |
| H(22A) | 6586 | 8861 | 2117 | 97 |
| H(22B) | 5892 | 9626 | 1809 | 97 |
| H(22C) | 6875 | 9513 | 1567 | 97 |
| H(23A) | 7660 | 8287 | 1248 | 119 |
| H(23B) | 7453 | 7311 | 932 | 119 |
| H(23C) | 7252 | 7570 | 1693 | 119 |
| H(24A) | 5530 | 6308 | −478 | 118 |
| H(24B) | 6378 | 6332 | 300 | 118 |
| H(24C) | 6549 | 6883 | −355 | 118 |
| H(25A) | 4448 | 7014 | −1242 | 128 |
| H(25B) | 3450 | 7416 | −1191 | 128 |
| H(25C) | 3782 | 6542 | −797 | 128 |
| H(26A) | 2638 | 7966 | −372 | 94 |
| H(26B) | 3030 | 8639 | −859 | 94 |
| H(26C) | 2891 | 8952 | −90 | 94 |
| H(5) | −150(20) | 6080(20) | 1661(17) | 60 |
| H(7) | 2140(20) | 5640(20) | 3781(17) | 61 |
| H(39A) | 1722 | 5047 | 1137 | 76 |
| H(39B) | 1556 | 5995 | 1412 | 76 |
| H(40A) | 41 | 5566 | 584 | 71 |
| H(40B) | 68 | 4610 | 879 | 71 |
| H(41A) | −1656 | 5480 | 793 | 74 |
| H(41B) | −1691 | 5626 | 1625 | 74 |
| H(42A) | −2274 | 4218 | 1365 | 73 |
| H(42B) | −1510 | 4036 | 906 | 73 |
| H(49A) | 2864 | 3387 | 1649 | 92 |
| H(49B) | 1846 | 3711 | 1736 | 92 |
| H(49C) | 2476 | 3079 | 2317 | 92 |
| H(50A) | 4159 | 2975 | 2812 | 142 |
| H(50B) | 5211 | 3456 | 3251 | 142 |
| H(50C) | 4822 | 3456 | 2371 | 142 |
| H(51A) | 5807 | 4442 | 4045 | 188 |
| H(51B) | 5937 | 5468 | 4134 | 188 |
| H(51C) | 6155 | 4983 | 3451 | 188 |
| H(52A) | 4316 | 7087 | 3675 | 164 |
| H(52B) | 5358 | 6695 | 3725 | 164 |
| H(52C) | 4807 | 6479 | 4330 | 164 |
| H(53A) | 2726 | 6889 | 3422 | 105 |
| H(53B) | 1906 | 6554 | 2670 | 105 |
| H(53C) | 2897 | 7093 | 2647 | 105 |
| H(60A) | −1981 | 4504 | 2684 | 85 |
| H(60B) | −2234 | 4046 | 3356 | 85 |
| H(60C) | −3039 | 3989 | 2557 | 85 |
| H(61A) | −2592 | 2595 | 3815 | 103 |
| H(61B) | −3147 | 1747 | 3345 | 103 |
| H(61C) | −3488 | 2674 | 3076 | 103 |
| H(62A) | −2695 | 581 | 2804 | 104 |
| H(62B) | −1891 | 872 | 3576 | 104 |
| H(62C) | −1563 | 346 | 2962 | 104 |
| H(63A) | −102 | 717 | 2503 | 113 |
| H(63B) | −466 | 924 | 1649 | 113 |
| H(63C) | −1186 | 363 | 1998 | 113 |
| H(64A) | −164 | 3064 | 1326 | 93 |
| H(64B) | −434 | 2063 | 1106 | 93 |
| H(64C) | 499 | 2363 | 1802 | 93 |
| H(77A) | 3080 | 4872 | 4588 | 98 |
| H(77B) | 2681 | 4272 | 3850 | 98 |
| H(77C) | 2188 | 4155 | 4502 | 98 |
| H(78A) | 951 | 5239 | 4640 | 108 |
| H(78B) | 1090 | 6154 | 4310 | 108 |
| H(78C) | 1999 | 5790 | 4924 | 108 |

Example 4

(Comparative Example # 1): HN5Zr(NMe$_2$)$_2$ 100 ml of hexane was added to 3.00 g (11.21 mmol) of (2) HN5 (HN(CH$_2$CH$_2$NHC$_6$(CH$_3$)$_5$)$_2$) and allowed to stir for ten minutes. Tetrakis(dimethylamino)zirconium (4.43 g, 11.21 mmol) was added to the slurry and left to stir for 19 hours. The heterogeneous solution was concentrated to half volume. The resulting tan precipitate was isolated by filtration and the remaining volatiles were removed by vacuum. Total yield of desired product was 5.14 g (80%). The kinetic parameters are listed in Table 5 below. $^1$H NMR (C$_6$D$_6$): δ 1.85 (br m, 1H), 2.14 (s, 6H), 2.20 (s, 6H), 2.22 (s, 6H), 2.24 (s, 6H), 2.50 (s, 6H), 2.53 (s, 6H), 2.68 (m, 4H), 3.04 (m, 2H), 3.12 (s, 6H), 3.37 (m, 2H).

Example 5

(Comparative Example #2): HN5ZrCl$_2$ 100 ml ether was added to a flask charged with 2.0 g (4.348 mmol) of (5) HN5Zr(NMe$_2$)$_2$. Next, 1.2 mL of chlorotrimethylsilane (9.1302 mmol) was added to the ether solution and allowed to stir for 19 hours. Volatiles were removed by vacuum and a tan powder remained. The powder was washed with hexane and filtered through a medium fritted filter. Recrystallization from toluene produced 1.53 g (63%) of the desired product. The kinetic parameters are listed in Table 5 below. $^1$H NMR (C$_6$D$_6$): δ 2.05 (s, 6H), 2.07 (s, 6H), 2.14 (s, 6H), 2.47 (s, 6H), 2.50 (s, 6H), 2.57 (m, 5H), 2.94 (m, 2H), 3.40 (m, 2H).

TABLE 5

Kinetic Parameters of Examples 1-5

|  |  | Productivity (gPE/mmol Zr/hr/100 psi) | kp (gPE/mmol Zr/hr/100 psi) | ki (min−1) | $t_{1/2}$ (min) |
|---|---|---|---|---|---|
| EX. 1: | HN5Zr(OC$_6$F$_5$)$_2$ | $1.2(1) \times 10^4$ | $2.3(1) \times 10^4$ | $3.0(9) \times 10^{-1}$ | $9(1) \times 10^1$ |
| EX. 2: | HN5Zr(OC$_6$F$_5$)$_2$ | $1.2(1) \times 10^4$ | $2.3(1) \times 10^4$ | $3.0(9) \times 10^{-1}$ | $9(1) \times 10^1$ |
| EX. 3: | HN5Zr(NMe$_2$)(OC$_6$F$_5$) | $9(2) \times 10^3$ | $2.0(4) \times 10^4$ | $2.0(6) \times 10^{-1}$ | $6(1) \times 10^1$ |
| EX. 4: | HN5Zr(NMe$_2$)$_2$ | $2.5(6) \times 10^3$ | $2.0(2) \times 10^4$ | $7(1) \times 10^{-1}$ | $1.0(1) \times 10^1$ |
| EX. 5: | HN5ZrCl$_2$ | $1.2(1) \times 10^4$ | $2.9(9) \times 10^4$ | $3(2) \times 10^{-1}$ | $7(2) \times 10^1$ |

General Procedure for Polymerization:

A computer controlled, one liter 316 stainless steel reactor with air-operated two-wing paddle and an inner steam-heated shell and an outer water-cooled shell was dried by heating to 135° C. while purging with 500 sccm of nitrogen for 30 minutes. After cooling to 50° C., it was charged with 600 mL hexane and 43 mL 1-hexene under inert conditions. A catalyst charging vessel comprising a ¼ inch (0.64 cm)×2" (5 cm) stainless steel tube isolated between two ball valves with a 25 mL stainless steel reservoir on top was charged with the polymerization catalyst in a drybox. A vessel atop this was charged with 5 mL dry hexane. The entire assembly was then attached to the reactor against a nitrogen purge. The reservoir containing hexane above the injection tube was pressurized to 250 psi with nitrogen. A solution of 100 micromoles of tri-isobutylaluminum (TIBA) and 2 mL 1-hexene was then added to the reactor and the reactor sealed. When the reactor reached conditions (130 psi ethylene, 85° C., 40 minutes), the catalyst was injected using the nitrogen pressure from the reservoir and held at conditions for the requisite time. The reaction was ended by venting and cooling.

Unless otherwise indicated, all numbers expressing quantities of ingredients, properties, reaction conditions, and so forth, used in the specification and claims are to be understood as approximations based on the desired properties sought to be obtained by the present invention, and the error of measurement, etc., and should at least be construed in light of the number of reported significant digits and by applying ordinary rounding techniques. Notwithstanding that the numerical ranges and values setting forth the broad scope of the invention are approximations, the numerical values set forth are reported as precisely as possible.

All priority documents are herein fully incorporated by reference for all jurisdictions in which such incorporation is permitted. Further, all documents cited herein, including testing procedures, are herein fully incorporated by reference for all jurisdictions in which such incorporation is permitted.

While the foregoing is directed to embodiments of the present invention, other and further embodiments of the invention may be devised without departing from the basic scope thereof, and the scope thereof is determined by the claims that follow.

We claim:

1. A catalyst system comprising a catalyst represented by the formula:

$$\alpha_a\beta_b\gamma_g MX_n$$

wherein M is a metal;

X is a halogenated aryloxy group;

β and γ are groups that each comprise at least one Group 15 atom;

α is a linking moiety that forms a chemical bond to each of β and γ;

a, b, g, and n are each integers from 1 to 4.

2. The catalyst system of claim 1, wherein the halogenated aryloxy group comprises a perfluorophenoxy group.

3. The catalyst system of claim 1, wherein the catalyst system is supported on a carrier.

4. The catalyst system of claim 1, wherein the catalyst system further comprises an activator.

5. The catalyst system of claim 1, wherein M is selected from the group consisting of titanium, zirconium, and hafnium.

6. The catalyst system of claim 1, further comprising one or more metallocene catalysts represented by the formula:

$$Cp^A Cp^B MX_n$$

wherein:

M is a metal atom;

$Cp^A$ and $Cp^B$ are each independently an unsubstituted or substituted cyclic ring group;

X is a leaving group; and n is zero or an integer from 1 to 4.

7. The catalyst system of claim 6, wherein $Cp^A$ and $Cp^B$ are each independently selected from the group consisting of cyclopentadienyl, indenyl, combinations thereof, and derivatives thereof.

8. The catalyst system of claim 6, wherein $Cp^A$ is a cyclopentadienyl group and $Cp^B$ is an indenyl group.

9. The catalyst system of claim 6, wherein $Cp^A$ is a cyclopentadienyl group and $Cp^B$ is an indenyl group and the one or more polymerization catalysts comprises a bridging group A, bridging $Cp^A$ and $Cp^B$.

10. The catalyst system of claim 6, wherein $Cp^A$ is a cyclopentadienyl group and $Cp^B$ is a cyclopentadienyl group.

* * * * *